US011479524B1

(12) United States Patent
Panchal et al.

(10) Patent No.: US 11,479,524 B1
(45) Date of Patent: *Oct. 25, 2022

(54) SYSTEM AND METHOD FOR SYNTHESIS OF DIALKYL CARBONATES USING CARBON DIOXIDE REACTION WITH METHANOL AND AMMONIA

(71) Applicant: E3TEC SERVICE, LLC, Hoffman Estates, IL (US)

(72) Inventors: Chandrakant B. Panchal, South Barrington, IL (US); Richard D. Doctor, Lisle, IL (US)

(73) Assignee: E3TEC SERVICES, LLC, Hoffman Estates, IL (US)

( * ) Notice: Subject to any disclaimer, the term of this patent is extended or adjusted under 35 U.S.C. 154(b) by 243 days.

This patent is subject to a terminal disclaimer.

(21) Appl. No.: 16/599,933

(22) Filed: Oct. 11, 2019

Related U.S. Application Data

(60) Provisional application No. 62/749,276, filed on Oct. 23, 2018.

(51) Int. Cl.
| | |
|---|---|
| *C07C 68/08* | (2006.01) |
| *B01D 3/14* | (2006.01) |
| *B01J 19/24* | (2006.01) |
| *B01D 53/22* | (2006.01) |
| *B01D 5/00* | (2006.01) |

(Continued)

(52) U.S. Cl.
CPC .............. *C07C 68/08* (2013.01); *B01D 3/009* (2013.01); *B01D 3/145* (2013.01); *B01D 3/324* (2013.01); *B01D 3/36* (2013.01); *B01D 5/006* (2013.01); *B01D 53/229* (2013.01); *B01J 19/245* (2013.01); *B01J 19/2475* (2013.01); *B01J 2219/24* (2013.01); *C07C 69/96* (2013.01)

(58) Field of Classification Search
CPC ......... C07C 68/04; C07C 68/08; C07C 69/96; B01D 3/143; B01D 3/145; B01D 3/02; B01D 3/009
See application file for complete search history.

(56) References Cited

U.S. PATENT DOCUMENTS 5,847,189 A * 12/1998 Tojo ...................... C07C 68/065
558/275
9,174,920 B1 * 11/2015 Panchal ................. B01D 3/009
(Continued)

*Primary Examiner* — Jonathan Luke Pilcher
(74) *Attorney, Agent, or Firm* — Rosenberg, Klein & Lee

(57) ABSTRACT

A method and system for membrane-assisted production of high purity concentrated dimethyl carbonate by the reaction of carbon dioxide and methanol is provided. Carbon dioxide is recovered from flue gas or other dilute streams from industrial processes by a membrane and subsequent conversion takes place to an intermediate methyl carbamate by reacting of carbon dioxide with ammonia and methanol. For high-purity carbon dioxide obtained by one of the carbon capture technologies or by a process (such as, for example, ethanol fermentation process) the membrane reactor is replaced with a catalytic reactor for direct conversion of carbon dioxide to methyl carbamate by reacting with ammonia and methanol. The methyl carbamate is further reacted with methanol for conversion to dimethyl carbonate. An integrated reactive distillation process using side reactors is used for facilitating the catalytic reaction in the subject method for producing high purity dimethyl carbonate.

17 Claims, 14 Drawing Sheets

(51) Int. Cl.
  *B01D 3/36*     (2006.01)
  *B01D 3/32*     (2006.01)
  *B01D 3/00*     (2006.01)
  *C07C 69/96*     (2006.01)

(56) References Cited

U.S. PATENT DOCUMENTS

| | | | | |
|---|---|---|---|---|
| 9,518,003 B1 * | 12/2016 | Panchal | ................ | C07C 68/065 |
| 9,796,656 B1 * | 10/2017 | Panchal | .................. | C07C 68/08 |
| 10,941,105 B1 * | 3/2021 | Panchal | ................ | B01D 5/006 |

* cited by examiner

SYSTEM AND METHOD FOR SYNTHESIS OF DIALKYL CARBONATES USING CARBON DIOXIDE REACTION WITH METHANOL AND AMMONIA

STATEMENT REGARDING FEDERAL SPONSORED RESEARCH OR DEVELOPMENT

This invention is made with government support under DE-SC0013233 awarded by the U.S. Department of Energy. The government has certain rights in the invention.

REFERENCE TO RELATED APPLICATIONS

This Utility Patent Application is based upon Provisional Patent Application No. 62/749,276 filed on 23 Oct. 2018.

INCORPORATION BY REFERENCE

U.S. Pat. No. 9,796,656 is incorporated herein by reference.

FIELD OF THE INVENTION

The subject invention is directed to synthesis of dialkyl carbonates, and particularly, to production of dimethyl carbonate (DMC) from methyl carbamate obtained by direct reaction of carbon dioxide ($CO_2$) with ammonia and methanol.

The subject invention is also directed to synthesis of dimethyl carbonate from methyl carbamate which is produced using either a membrane reactor for recovery and conversion of $CO_2$ to alkyl carbamate (methyl carbamate), or using a catalytic reactor for reacting high-purity $CO_2$ captured using a commercial process (for example, the Amine process, or ethanol fermentation process) and converting the high-purity $CO_2$ to methyl carbamate.

The subject invention is further directed to synthesis of methyl carbamate which integrates the membrane reactor in the process. The membrane functions to capture $CO_2$ from a dilute stream, and $CO_2$ diffuses through the membrane surface and reacts with the flowing reactants ammonia and methanol. The simultaneous $CO_2$ capture from combustion flue gas and other $CO_2$ streams and conversion to methyl carbamate followed by conversion of methyl carbamate to dimethyl carbonate is the essential part of the subject process.

In addition, the present invention is directed to an improved process for methyl carbamate synthesis (which is an intermediate stage for production of dimethyl carbonate) which avoids a conventional energy consuming reaction of methanol with urea.

The subject invention also addresses a synthesis process of dimethyl carbonate which uses two distillation columns for achieving high-concentration pure dimethyl carbonate (DMC) with lower energy consumption.

BACKGROUND OF THE INVENTION

Dialkyl carbonates cover a group of extensively exploited safe "green" reagents and solvents. Dimethyl carbonate and methyl carbonates are included in the dialkyl carbonates group, and can be produced using dimethyl and methyl carbamates. Methyl carbamate is used in textile industries as a reactive intermediate, as well as in the manufacture of pharmaceuticals, insecticides, and urethane.

Dimethyl carbonate and methyl carbamate represent important building blocks in many commercial products. In particular, applications of dimethyl carbonate include production of polycarbonates, such as electrolytes in lithium-ion batteries, chemical intermediates in production of polyurethane and low-volatile solvents.

Commercially, methyl carbamate is produced by reacting methanol with urea, or, alternatively, by reacting ammonia with dimethyl carbonate. Both commercial processes require initial expensive and energy consuming production of urea and dimethyl carbonate, which are subsequently converted back by a reverse chemical process.

Conventionally, Amine-process-based recovery of carbon dioxide ($CO_2$) from a raw natural gas is practiced, for example, using systems for carbon dioxide recovery from combustion flue gases. In these systems, carbon dioxide is absorbed from the combustion flue gas and subsequently recovered from the rich Amine stream by stream stripping.

Emerging carbon dioxide capture technologies include: a) membrane separation; b) alternate solvent to Amines; c) solid adsorbent; and d) non-aqueous solvents (presented in the DOE/NETL Project Review Proceedings, DOE/NETL Project Review Proceedings http:/www.netl.doe.gov/events/conference-proceedings/2018/2018-netl-co2-capture-technology-project-review-meeting).

Unfortunately, the conventional direct conversion of carbon dioxide to DMC using different catalysts has significant limitations, as shown, for example, by Tamboli, et al., ("Catalytic Development in the Direct Dimethyl Carbonate Synthesis from Carbon Dioxide and Methanol," Chemical Engineering Journal, 33, pp. 530-544, 2017), and Kabra, et al, ("Direct Synthesis of Dimethyl Carbonate from Methanol and Carbon Dioxide: A Thermodynamic and Experimental Study," J. of Supercritical Fluids, 117, pp. 98-107, 2016).

Thermodynamic limitations of the direct conversion of $CO_2$ to alkyl carbonates require extreme operating conditions. These conditions include high pressure, high temperature, and critical fluid conditions. Even under such reaction conditions, the conversion is relatively low, which requires recycling a large fraction of unreacted reagents.

Unless innovative catalysts are developed for the reaction to occur at moderate conditions with high conversion rate, the direct conversion of $CO_2$ to alkyl carbonates is expected to be limited to scientific studies prevented from advancing to commercial plants.

Therefore, it would be desirable to develop a process using chemical carriers, such as, for example, ammonia, to form an intermediate stage preceding the stage of synthesis of dialkyl carbonates.

PRIOR ART

U.S. Pat. No. 9,796,656, describes a method for producing high-concentration alkyl carbonates using $CO_2$ as feedstock, in accordance with which methyl carbamate is synthesized by reacting urea with methanol. Urea is produced commercially by reacting carbon dioxide with ammonia.

The result of the urea-methanol reaction, i.e., methyl carbamate, is subsequently reacted with methanol to produce dimethyl carbonate using a heat integrated reactive distillation process equipped with side reactors and permeation-vaporization (PerVap) membranes for separation of the azeotropic mixture of methanol and dimethyl carbonate.

Wang, et al., reported in "Modeling of the Catalytic Distillation Process for the Synthesis of Dimethyl Carbonate by Urea Methanolysis Method", Ind. Eng. Chem. Res. 46, pp. 8972-8979 (2007), the application of conventional reactive distillation (RD) for production of dimethyl carbamate from urea and methanol. The process is based on a single column containing a rectifying section, a reaction section, and a stripping section operated at a pressure approximately 9-13 times of the atmospheric pressure.

The reaction section of the column in question is packed with zinc oxide catalyst, and the exterior walls are locally heated in the reaction section to maintain a temperature in the reaction zone within the column at approximately 180° C. which is about 40-50° C. higher than the temperature in the rectifying or stripping sections. Methanol is co-fed with urea in a pre-reactor whose effluent is fed to the rectification section of the conventional RD column. Additional fresh methanol is fed to the stripping section below the reaction zone with a total methanol:urea molar ratio of 19.4:1. The methanol:urea stoichiometric ratio for this reaction is 2:1.

This process produces a low-purity (less than 10 wt. % of DMC in methanol) DMC product stream at low conversion rates (25-40%). Higher reaction temperatures would be required for higher conversions. However, this can only be achieved with conventional RD column by raising operating pressures, thus resulting in higher capital costs.

DMC (dimethyl carbonate) and methanol form a homogeneous azeotropic mixture over a wide range of pressures rendering it difficult to separate the two components without the addition of a third component as an entrainer. However, an efficient process would require an operation in a fashion that would permit the separation of DMC from other components in the system without the need for an entrainer.

It therefore would be highly desirable to provide a dialkyl carbamates synthesis process free from shortcomings of conventional processes to overcome the need for ammonia acting as entrainer to partially break the azeotrope mixture of DMC and methanol.

SUMMARY OF THE INVENTION

It therefore is an object of the present invention to provide a process and system for synthesis of dialkyl carbonates (such as dimethyl carbonate) from dimethyl carbamates obtained by direct reaction of $CO_2$ with ammonia and methanol where $CO_2$ is captured from combustion flue gas and various $CO_2$ streams in an efficient manner.

It is another object of the present invention to provide a process and system for recovery of $CO_2$ and conversion of $CO_2$ to DMC using a membrane reactor.

It is an additional object of the present invention to provide a system and method for conversion of a high-purity captured $CO_2$ to DMC using a catalytic reactor.

Also, it is an object of the present invention to provide a process for conversion of $CO_2$ to dyalkyl carbonates using two distillation columns (to decouple the reaction distillation column from the product distillation column), which would be operated at a higher pressure for breaking the azeotrope mixture of DMC and methanol using permeation-vaporization (PerVap) membranes capable of selective separation of methanol to attain high-concentration of the produced pure DMC.

It is still an object of the present invention to provide a method for producing concentrated dimethyl carbonate (DMC) composition by a direct reacting of carbon dioxide ($CO_2$) with ammonia and methanol thus eliminating production of urea followed by the urea-methanol reaction.

Another object of the present invention is to provide a process and system for direct conversion of carbon dioxide ($CO_2$) into dimethyl carbonate (DMC) in two alternative fashions: (a) in one embodiment, using a membrane reactor that captures carbon dioxide from combustion flue gases and other dilute sources, where carbon dioxide diffuses through the membrane and reacts with methanol and ammonia flowing on the other side of the membrane surface, and (b) in an alternate embodiment, using a catalytic reactor (instead of the membrane reactor) for conversion of substantially pure carbon dioxide to DMC, where $CO_2$ is captured through industrial processes.

It is a further object of the present invention to provide a system and method for DMC synthesis which uses two thermally coupled distillation columns following the membrane or catalytic reactor, where the resulting product stream from the membrane reactor, or the catalytic reactor, consisting of methyl carbamate and unreacted methanol and ammonia, is inserted into the first of the two thermally coupled distillation columns. Unreacted ammonia and methanol carrying portion of dimethyl carbonate product is drawn from the first distillation column and is inserted into an ammonia stripping column for recovery and recycling ammonia to the membrane or catalytic reactor to increase the yield of a concentrated methyl carbamate.

In the subject system and process, a mixture of dimethyl carbonate and methyl carbamate, as well as the unreacted methanol is drawn from the first distillation column and is passed through a side reactor, thus producing a more concentrated dimethyl carbonate composition. The concentrated dimethyl carbonate is subsequently returned to the first distillation column. This step is repeated for a plurality of side reactors for production of a further concentrated dimethyl carbonate.

A concentrated vapor stream of dimethyl carbonate is side drawn form a middle section of the first distillation column. The concentrated vapor stream is condensed and inserted into a PerVap for selective separation of methanol, which is returned into the reactor (membrane or catalytic) and/or one or more side reactors.

The resulting stream of dimethyl carbonate from the first distillation column is inserted into the second distillation column for producing high-concentration pure dimethyl carbonate as a bottom product of the second distillation column. The methanol recovered from the upper section of the second distillation column is further recycled.

The subject invention particularly addresses the step of catalytic conversion of carbon dioxide to methyl carbamate by reacting methanol and ammonia as depicted by chemical reaction presented by (Eq. 1)

$$NH_3 + CO_2 + CH_3OH \leftrightharpoons NH_2-O-CO-CH_3 + H_2O \quad \text{(Eq. 1)}$$

wherein $NH_3$ is Ammonia, $CO_2$ is Carbon-dioxide, $CH_3OH$ is Methanol, $NH_2-O-CO-CH_3$ is Methyl carbamate, and $H_2O$ is water.

By removing the produced water using the PerVap membrane, the reaction continues to favor conversion to methyl carbamate.

Methyl carbamate can be further reacted with methanol to synthesize dimethyl carbonate (DMC) and to release ammonia as depicted by the chemical reaction presented by (Eq. 2).

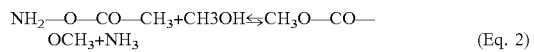
$$NH_2-O-CO-CH_3 + CH3OH \leftrightharpoons CH_3O-CO-OCH_3 + NH_3 \quad \text{(Eq. 2)}$$

where $NH_2-O-CO-CH_3$ is Methyl Carbamate, $CH_3OH$ is Methanol, $CH_3O-CO-OCM_3$ is Dimethyl Carbonate, and $NH_3$ is Ammonia.

This chemical reaction (Eq. 2) is addressed in U.S. Pat. No. 9,796,656, (incorporated herein by reference in its entirety), where methyl carbamate is derived by reacting urea with methanol.

Urea typically is produced commercially by reacting carbon dioxide ($CO_2$) with ammonia. The present system/method bypasses the urea step, which unfortunately is energy and cost intensive, by using a direct reaction of carbon dioxide, methanol and ammonia to form methyl carbamate and water (as presented in Eq. 1). Water is removed from the product stream in the subject process.

DMC is further reacted to form methyl-ethyl carbonate by partial transesterification with ethanol (as presented in Eq. 3) releasing one molecule of methanol that can be recycled.

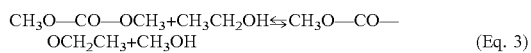
(Eq. 3)

where $CH_3O-CO-OCH_3$ is Dimethyl Carbonate, $CH_3CH_2OH$ is Ethanol, $CH_3-CO-OCH_2CH_3$ is Methyl-Ethyl Carbonate, and $CH_3OH$ is Methanol.

Complete transesterification with ethanol yields diethyl carbonate (as presented in Eq. 4) releasing two molecules of methanol that can be recycled. These two forms of dialkyl carbonates have broad applications, including, for example, an electrolyte in lithium-ion batteries.

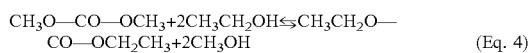
(Eq. 4)

where $CH_3O-CO-OCH_3$ is Dimethyl Carbonate, $CH_3CH_2OH$ is Ethanol, $CH_3CH_2O-CO-OCH_2CH_3$ is Diethyl Carbonate, and $CH_3OH$ is Methanol.

In one aspect, the present invention addresses a method for synthesis of dimethyl carbonate which comprises the following steps:

(a) establishing a system including a reactor which may be a membrane reactor or a catalytic reactor. Two-column distillation system is coupled to the reactor.

(b) capturing and supplying carbon dioxide ($CO_2$) into the reactor, (c) feeding methanol and ammonia into the reactor, and (d) reacting the captured carbon dioxide ($CO_2$) with the methanol and ammonia in the reactor, thus forming a product including dimethyl carbonate, unreacted methanol, unreacted ammonia, methyl carbamate, and combination thereof, (e) feeding the product from the reactor into the two-column distillation system, (f) separating and recovering the unreacted ammonia from the two-column distillation system, and recycling to the reactor to increase yield of concentration dimethyl carbonate, (g) recycling the dimethyl carbonate, methyl carbamate, and unreacted methanol from the two-column distillation system to an input thereof, thus producing a concentrated dimethyl carbonate, (h) separating and recovering unreacted methanol from the two-column distillation system and recycling the recovered methanol to the reactor, and (i) separating the concentrated dimethyl carbamate and recycling via the two-column distillation system, thus obtaining a high-concentrated and pure dimethyl carbonate product.

The method further comprises the steps of in the step (b), capturing carbon dioxide from combustion flue gas or dilute industrial process stream for the reaction in the membrane reactor, and utilizing high-purity captured carbon dioxide for the reaction in the catalytic reactor.

In step (a), a separating unit is connected to an output of the reactor, and the product from the reactor is fed into the separation unit to separate water therefrom.

In the method, the two-column distillation system is configured with a reaction column, operatively coupled to an output of the reactor, and a product distillation column operatively coupled to an output of the reaction distillation column. The reaction distillation column of the two-column distillation system is fed with the product from the output of the reactor.

The method further continues with operatively coupling an ammonia rectification column to an output of the reaction distillation column, and recycling the ammonia from the output of the reaction distillation column to the ammonia rectification column, thus producing rectified ammonia.

The rectified ammonia from the ammonia rectification column is recycled into the reactor, and the rectified ammonia reacts with carbon dioxide and methanol in the reactor, thus producing methyl carbamate.

The method further comprises operatively coupling at least one side catalytic reactor to the ammonia rectification column, recycling the mixture of methyl carbamate, and unreacted methanol from the reaction distillation column through one or more side catalytic reactors, thus producing the concentrated dimethyl carbonate, and returning the concentrated dimethyl carbonate to the reaction distillation column, at least two times, thus recovering the concentrated dimethyl carbonate.

The subject method further includes the steps of:
operatively coupling a separation unit to the reaction distillation column, and
condensing the mixture containing the concentrated dimethyl carbonate in the vapor phase and subsequently feeding the mixture containing the condensed concentrated dimethyl carbonate into the separation unit for selective separation of methanol from the mixture containing condensed concentrated dimethyl carbonate for recycle;

feeding a stream containing dimethyl carbonate from the separation unit into the product distillation column to produce the highly-concentrated dimethyl carbonate product, and
condensing and feeding the stream from the product distillation into the separation unit for selective separation of methanol for recycle.

The subject method further comprises the steps of:
feeding the concentrated dimethyl carbonate composition from the at least one side catalytic reactor into the product distillation column below a location in the product distillation column where the product mixture is drawn to the at least one side catalytic reactor,
passing the concentrated dimethyl carbonate composition through a plurality of distillation stages in the product distillation column from a top stage towards a lower stage of the product distillation column, and
cycling the concentrated dimethyl carbonate composition in the vapor phase through the product distillation column a plurality of cycles for producing the highly-concentrated and pure dimethyl carbonate product.

The subject invention also addresses a system for producing dimethyl carbonate. The subject system comprises:
a reactor selected from a group consisting of a membrane reactor and a catalytic reactor,
a source of carbon dioxide ($CO_2$) coupled to an input of the reactor,
a source of reactants including methanol and ammonia coupled to the input of said reactor,
a reaction distillation column operatively coupled to an output of the reactor, and
a product distillation column operatively coupled to an output of the reaction distillation column and thermally coupled thereto, an ammonia rectification unit coupled to the reaction distillation unit, one or more side catalytic reactors operatively coupled a bottom stage of the reaction distillation column, and a separation unit operatively coupled between the reaction distillation column and the product distillation column, wherein the $CO_2$ reacts with the methanol and ammonia in the reactor, thus forming a product mixture of methyl carbamate, unreacted ammonia, unreacted methanol, and low-level dimethyl carbonate, wherein the product mixture is fed from the reactor into the reaction distillation column, wherein the product mixture is drawn from an upper stage of the reaction distillation column into the ammonia rectification unit to separate ammonia contained in the product mixture, and to recycle said separated ammonia into the reactor for further reaction with carbon dioxide and methanol and formation of methyl carbamate, wherein a methanol-rich bottom product of said reaction distillation column is fed into the side catalytic reactor or into the product distillation column for converting the methyl carbamate into concentrated dimethyl carbonate, and wherein the separation unit selectively separates methanol from the methanol-rich bottom product of the reaction distillation column prior to feeding the methanol-rich bottom product to the product distillation column, wherein the separated methanol returns to the reactor, and wherein the concentrated dimethyl carbonate in the product distillation column is recycled through the product distillation column a plurality of cycles for increasing concentration and pureness thereof.

These and other objects and advantages of the subject invention will be more apparent in view of the detailed description of the preferred embodiment(s) taken in conjunction with the Patent Drawing Figures.

DESCRIPTION OF THE PREFERRED EMBODIMENT(S)

Figure 1:
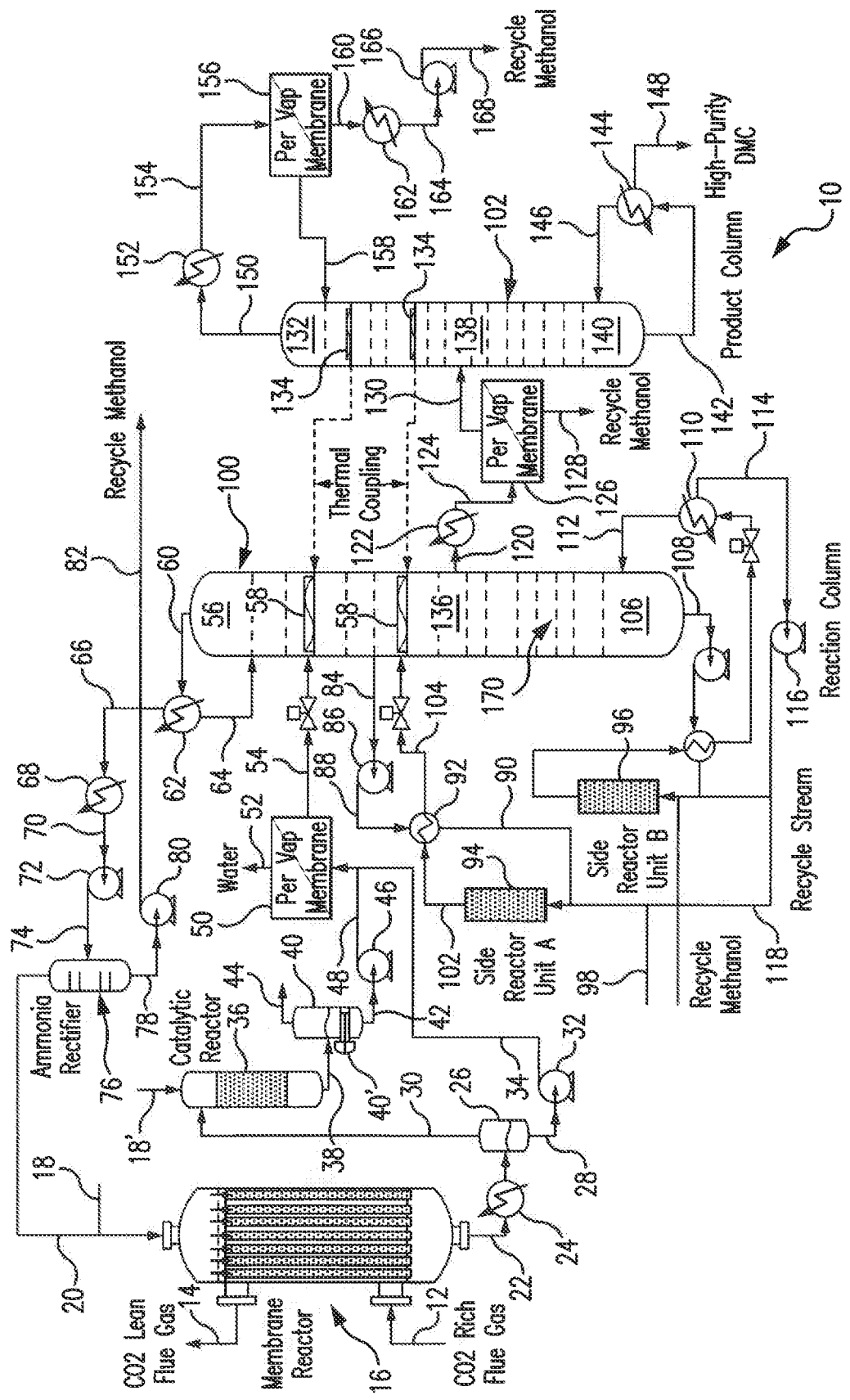
FIG. 1 is a schematic flow diagram of the subject membrane-assisted alkyl-carbonate process for dilute sources of carbon dioxide.
Figure 2:
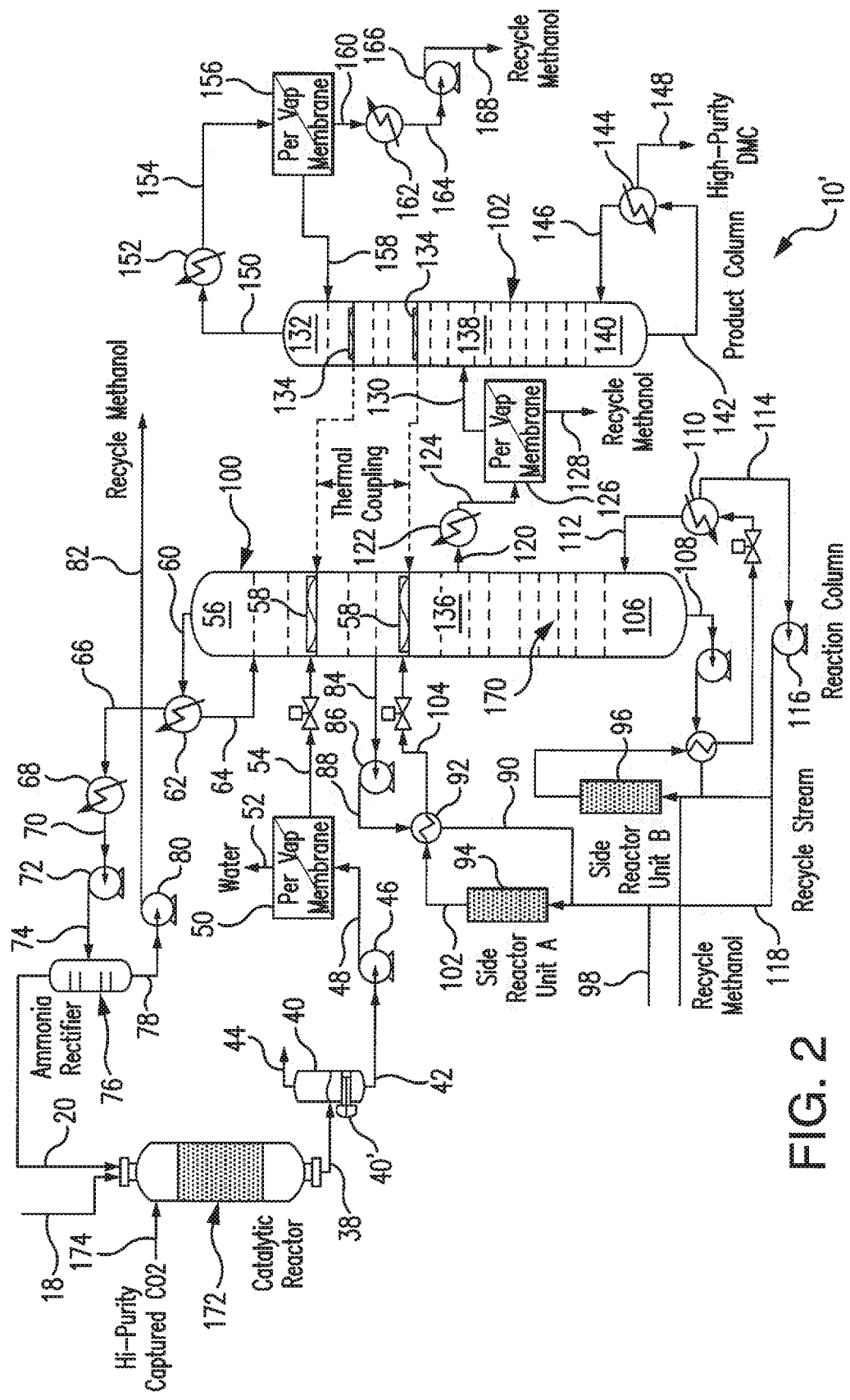
FIG. 2 is a schematic flow diagram of the catalytic direct conversion process for high-purity captured carbon dioxide.
Figure 3:
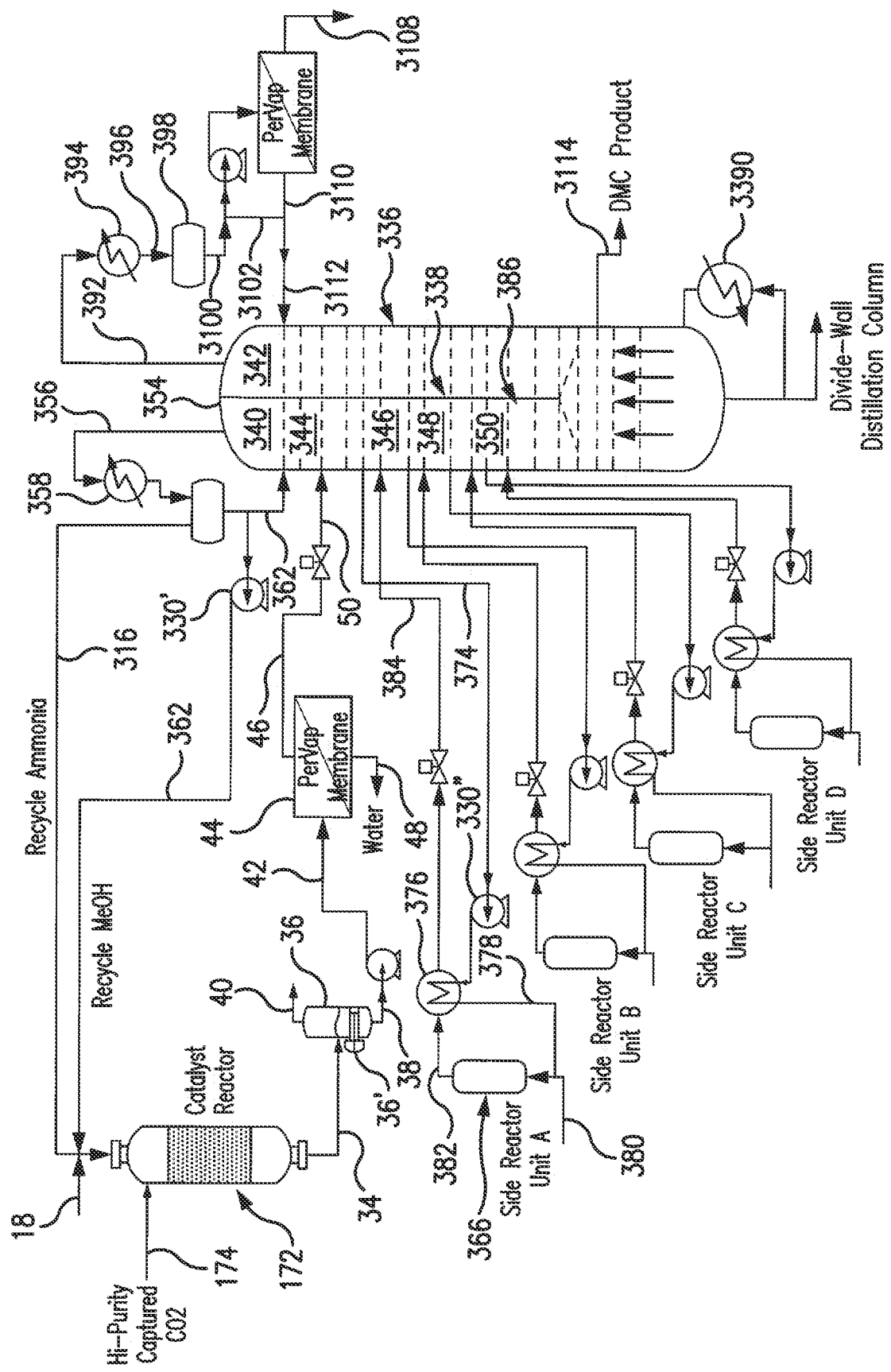
FIG. 3 is a schematic flow diagram of the catalytic direct conversion process for the divided-wall column.

The subject process for producing purified and concentrated dimethyl carbonate, as illustrated in FIGS. 1-3, uses carbon dioxide ($CO_2$) as feed stock. In the present process, carbon dioxide ($CO_2$) is either captured from a flue gas using a membrane reactor, or, alternatively, concentrated carbon dioxide is used which is captured by one of the commercial processes, such as, for example, the Amine absorption process.

As shown in FIGS. 1-3, a reactive distillation column is equipped in the subject process with side reactors, and the permeation-vaporization (PerVap) membrane is integrated with either a membrane reactor or a catalytic reactor for direct conversion of carbon dioxide by reacting with ammonia and methanol.

The subject system 10, as shown in FIG. 1, is designed for synthesis of alkyl carbonates using carbon dioxide recovered from flue stream 12 gases using a membrane reactor system 16. The $CO_2$ rich flue gas 12 enters the membrane reactor 16. Subsequently, $CO_2$ is recovered from the flue gas 12, and reacts with methanol and ammonia to form methyl carbamate, which is an intermediate for synthesis of dimethyl carbonate. The carbon dioxide lean stream 14 exits from the membrane reactor 16 after $CO_2$ is recovered from the flue gas 12 in the membrane reactor 16.

As shown in FIG. 1, the recycled ammonia ($NH_3$) is fed to the membrane reactor 16 via the recycled ammonia feed line 20. Recycled methanol ($CH_3OH$) is fed from lines 168 and 128 along with fresh methanol via the recycled methanol line 18 and is mixed with the recycled ammonia line 20.

The mixture of streams 18 and 20 can be in the liquid or the vapor phase before entering into the membrane reactor 16. Carbon dioxide permeating though the membrane in the membrane reactor 16 reacts with ammonia and methanol entered via the streamlines 18 and 20.

The resulting product methyl carbamate (produced in the membrane reactor 16), as well as dimethyl carbonate, and the unreacted ammonia and methanol exit the membrane reactor 16 via the streamline 22. If the stream exiting via the line 22 is in the vapor phase, it is condensed by a condenser 24.

The vapor-liquid phases generated in the condenser 24 are separated in the flash tank 26. The liquid phase 28 exiting the flash tank 26 is pumped by a pump 32 via a streamline 34 towards the PerVap membrane 50 to selectively separate the byproduct water via the streamline 52.

The vapor phase streamline 30 from the flash tank 26 enters into a finishing catalytic reactor 36 for further reacting unreacted carbon dioxide with recycled ammonia and methanol entering via the stream 18'.

The product stream 38 from the catalytic reactor 36 is fed into the flash tank 40 which is cooled by a cooler 40' entering into tank 40 in order to maximize recovery of products in the liquid phase.

A residual unreacted carbon dioxide and an inert gas, such as nitrogen, is purged via the streamline 44. The product liquid stream 42 is pumped by the pump 46 via the streamline 48 to the PerVap membrane 50 along with stream 34 (liquid phase) to selectively separate the byproduct water which is condensed and recover via the streamline 52.

The product stream 54 from the PerVap membrane 50 consist of methyl carbamate and unreacted methanol and ammonia. The product stream 54 is fed to the distillation column (or the reaction column) 100. The reaction distillation system 100 includes a plurality of recycling components supporting the reactions which result in a purified and concentrated dimethyl carbonate exiting from a product distillation column 102 via the dimethyl carbonate product line 148.

The methyl carbamate (which is the product of the conversion of $CO_2$ in the membrane reactor 16) is converted to dimethyl carbonate by way of the multiple, for example, two side reactors 94 and 96. More or less than two side reactors may be used in the present system 10, including the one connected to the bottom of the distillation column (reaction distillation column) 100. As an example, only one flow process for one of the side reactors will be further described for the sake of brevity of description.

With respect to the process associated with the side reactor 94, a product stream is drawn from one of the stages of the distillation column 100 which flows through the product streamline 84 to the pump 86 which enters the product stream into the heat exchanger 92. The heat exchanger 92 recovers heat from product streams for pre-heating the feed for improved energy efficiency of the overall process.

Subsequent to the passage of the product stream through the heat exchanger 92, the products stream enters into the side reactor 94 along with the recycle methanol stream 98 and the recycle stream 118 from the bottom of the distillation column 100.

The produced methyl carbamate is subsequently converted to dimethyl carbonate in the side reactor 94 and exits therefrom via the product line 102 for passage through the heat exchanger 92, and re-enters into the distillation column 100 on the line 104.

It is to be understood that multiple side reactors may be used in the subject system for achieving a desired conversion of methyl carbamate to dimethyl carbonate. The conversion to the final product may be by the use of reactive distillation stages 170 of the distillation column 100.

Although only one reactive distillation stage 170 is shown, it is to be understood that a number of stages 170 may be used. Catalysts on the reactive distillation stages 170 may either be incorporated on distillation trays or packed columns.

As is seen in FIG. 1, the product streams returning via the re-entry product lines 104 are inserted into the distillation column (reaction distillation column) 100 one stage lower than the withdrawal stage represented by the product line 84. Distillation stages where the product streams are introduced into the reaction distillation column 100 are equipped with thermal devices 58. The thermal devices 58 may be incorporated on distillation trays or within packed columns. Thermal devices 58 are thermally coupled with the thermal devices 134 of the product distillation column 102 for recovering heat energy from the distillation column (or product column) 102 operating at a higher temperature than the temperature of the reaction distillation column 100. A well-known heat transfer fluid system, or a heat pipe, may be used to transfer the heat energy from the distillation column 102 to the distillation column 100.

A product mixture consisting of unreacted methyl carbamate and dimethyl carbonate accumulates in the bottom portion 106 of the distillation column 100 and is fed to the side reactor via the streamline 108 for further conversion of residual methyl carbamate. The product stream is returned to the heat exchanger (reboiler) 110. Dimethyl carbonate along with unreacted methanol is vaporized in through the reboiler 110. Vapor phase dimethyl carbonate along with methanol in the vapor phase re-introduced into the distillation column 100 via the streamline 112.

The liquid product stream 114 containing unreacted methyl carbamate from the reboiler 110 is fed to the pump 116 for recycling to side reactors via the streams 118 for further conversion to dimethyl carbonate.

A product mixture consisting primarily of methanol and ammonia with some fraction of dimethyl carbonate in the top portion 56 of the distillation column 100 and fed to the heat exchanger 62 (overhead partial condenser) via the streamline 60. Volatile ammonia and methanol, in the vapor phase, are subsequently fed to the heat exchanger 68 for condensing fully before entrance into the ammonia rectification column 76 aided by the pump 72 via the streamline 74.

The liquid product from the heat exchanger 62 with recovered dimethyl carbonate is returned via the line 64 to the first stage of the distillation column 100.

Ammonia recovered from the ammonia rectification column 76 is recycled into the membrane reactor either in the liquid or the vapor phase via the streamline 20.

The bottom product of the ammonia rectification column 76 is pumped by the pump 80 to a reservoir tank for methanol recycle or to the product distillation column 102 via the streamline 82 for recovery of dimethyl carbonate carried over by methanol.

As seen in FIG. 1, a vapor-phase product stream with a high concentration of dimethyl carbonate is withdrawn from one of the intermediate stages 136 (in the reaction column 100) and is fed into the heat exchanger 122 via the streamline 120. The product stream 120 is fully condensed and is fed into the PerVap membrane 126 via the streamline 124 for a selective separation of high-concentration methanol that is recycled to the side reactors 94, 96 and the membrane reactor 16 via the streamline 128.

The concentrated dimethyl carbonate stream is fed into the distillation column (product column) 102 via stream 130 on one of the intermediate stages 138. The distillation column 102 (product column) operates at higher pressure to effectively separate methanol from dimethyl carbonate (from the azeotrope of methanol and dimethyl carbonate).

Product stream 142 with a high-concentration of dimethyl carbonate is withdrawn from the bottom portion 140 of the distillation column 102 and is fed into the heat exchanger (reboiler) 144 for vaporizing a small fraction of methanol that may have been carried down the distillation column 102 and fed back into the distillation column 102. The purified high-concentration dimethyl carbonate is withdrawn via the line 148 of the product column 102 as a final product.

A methanol-rich product stream 150 is withdrawn from the top portion 132 of the distillation column 102 and is fully condensed by the heat exchanger (overhead condenser) 152. The condensed product stream 154 is fed into the PerVap membrane 156 for selective separation of methanol for recycling to side reactors 94 and 96 and the membrane reactor 16 via streamline 168. The stream 158 is retuned into the first stage of the distillation column 102 as a reflux.

FIG. 2 is representative of another embodiment of the subject system 10' using the catalytic reactor process for direct conversion of high-purity $CO_2$ to DMC. The system shown in FIG. 2 thus does not use the membrane reactor 16 and associated components presented in FIG. 1. The high-purity captured carbon dioxide is captured by one of the commercial or emerging carbon capture technologies. High-purity captured carbon dioxide is fed to the top of the catalytic reactor 172, which is a downflow catalytic reactor, referred to herein as a trickle-bed reactor. The combined stream of recycled and fresh methanol stream 18 and recycle ammonia stream 20 are also fed to the top. The combined feed stream of methanol 18 and ammonia 20 can be in liquid or vapor phase. The product stream 38 containing methyl carbamate along with the unreacted ammonia and methanol are fed to the flash tank 40. The subsequent process following the catalytic reactor 172 is identical to that shown in FIG. 1.

Referring to FIG. 3, the urea process used in the system presented in U.S. Pat. No. 9,796,656 has been replaced by the catalytic reactor 172 for direct conversion of the captured high-purity carbon dioxide by reacting with methanol and ammonia. The catalytic reactor 172 is identical to the one presented in FIG. 2. The remaining part of the process is identical to that shown in U.S. Pat. No. 9,796,656 with stream and component numbers having an added pre-number 3. For example, for the column 36 number 336 is used in FIG. 3 similar numbering has been used to other elements as well.

Figure 4:
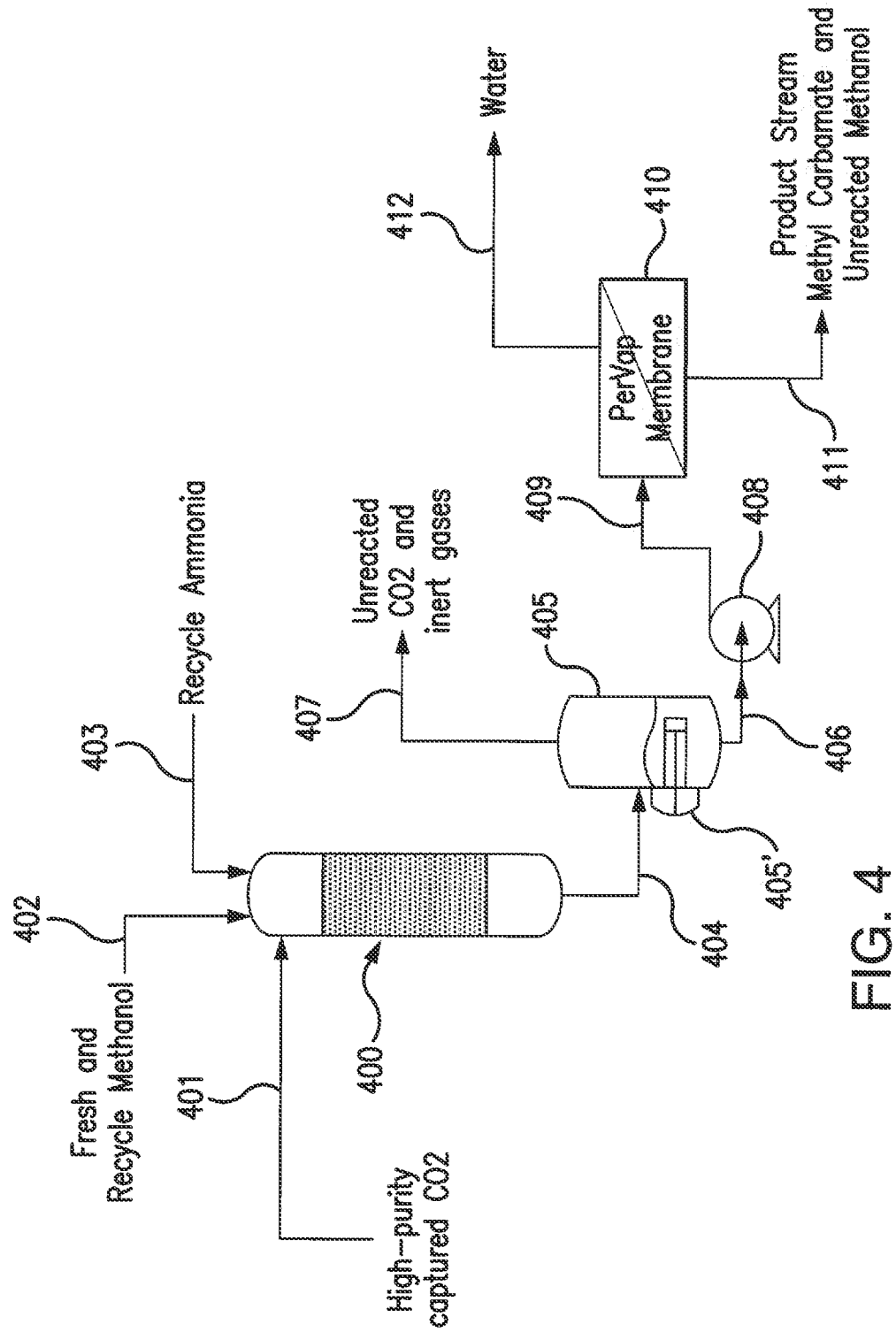
FIG. 4. is a schematic representation of the catalytic reactor with down-flow of reactants integrated with permeation-vaporization (PerVap) membrane.
Figure 5:
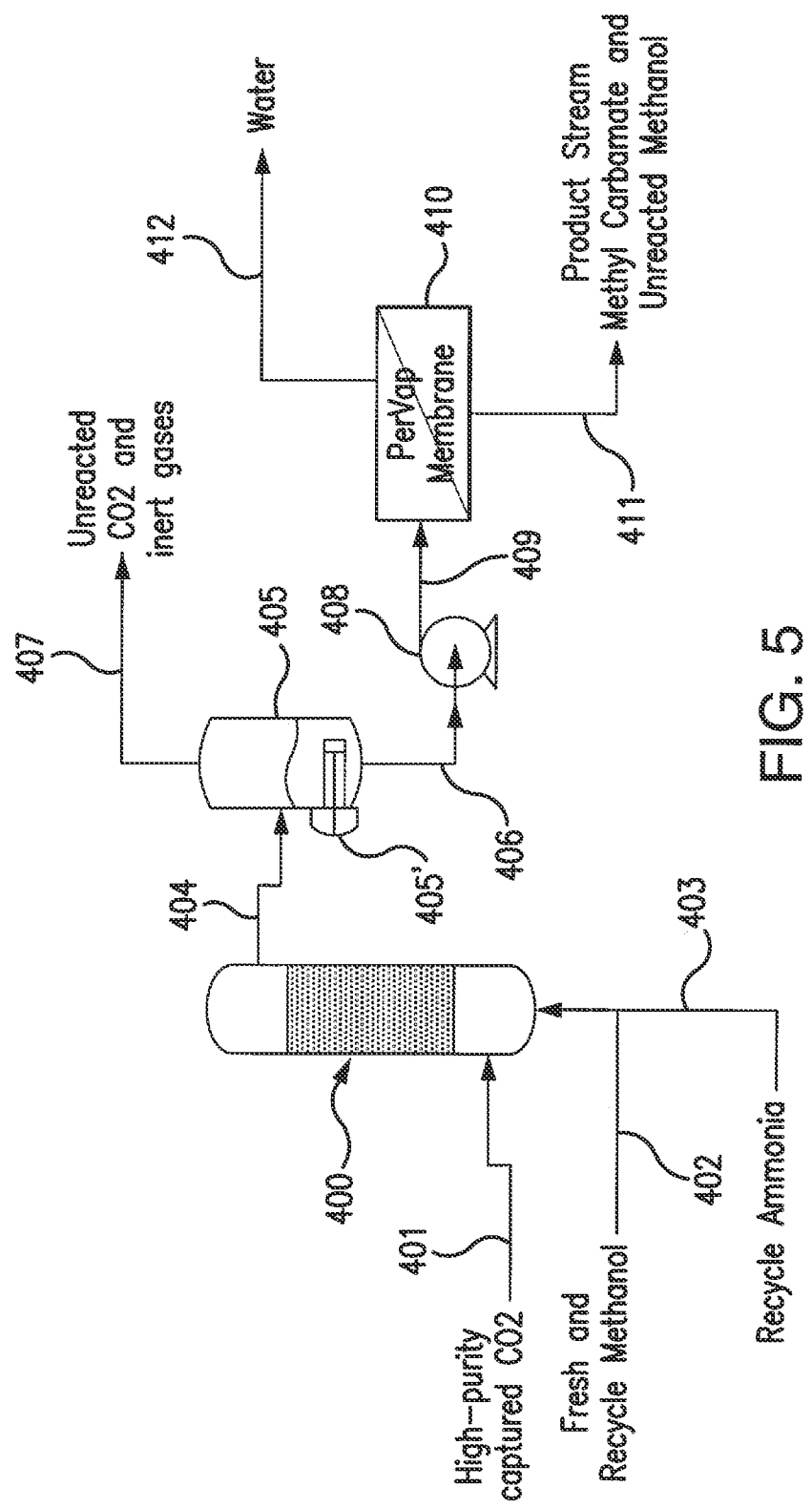
FIG. 5. is a schematic representation of the catalytic reactor with up-flow of reactants integrated with PerVap membrane.

Referring now to FIGS. 4 and 5, a two flow configuration of the catalytic reactor containing packed-bed catalyst are presented. FIG. 4 is representative of the catalytic reactor 400 with high-purity carbon dioxide entering via the stream 401. The reactant (methanol) on the stream 402 and ammonia is fed on the stream 403 into the catalytic reactor 400 from the top 12 in a trickle-bed reactor configuration. Reactants streams 402 and 403 can be in the liquid or the vapor phase.

Product methyl carbamate along with unreacted ammonia, methanol and carbon dioxide flows downward and exit from the bottom of the catalytic reactor 400 via the stream 404, and is fed therefrom into the flash tank 405.

Heat exchanger 405' is mounted inside the flash tank 405 to condense and cool the product for recovery of methyl carbamate while purging unreacted carbon dioxide and the inert gas (such as nitrogen).

The liquid stream 406 is pumped by the pump 408 though the PerVap membrane 410 for selective separation of byproduct water on the streamline 412. The product stream containing carbamate and unreacted methanol is fed to the distillation column for conversion to dimethyl carbonate.

FIG. 5 is shown with the same catalytic reactor 400 with carbon dioxide and reactants methanol and ammonia fed from the bottom of the catalytic reactor 400. This catalytic reactor configuration is called flow-reactor, which can be packed-bed or fluidized-bed reactor.

Figure 6:
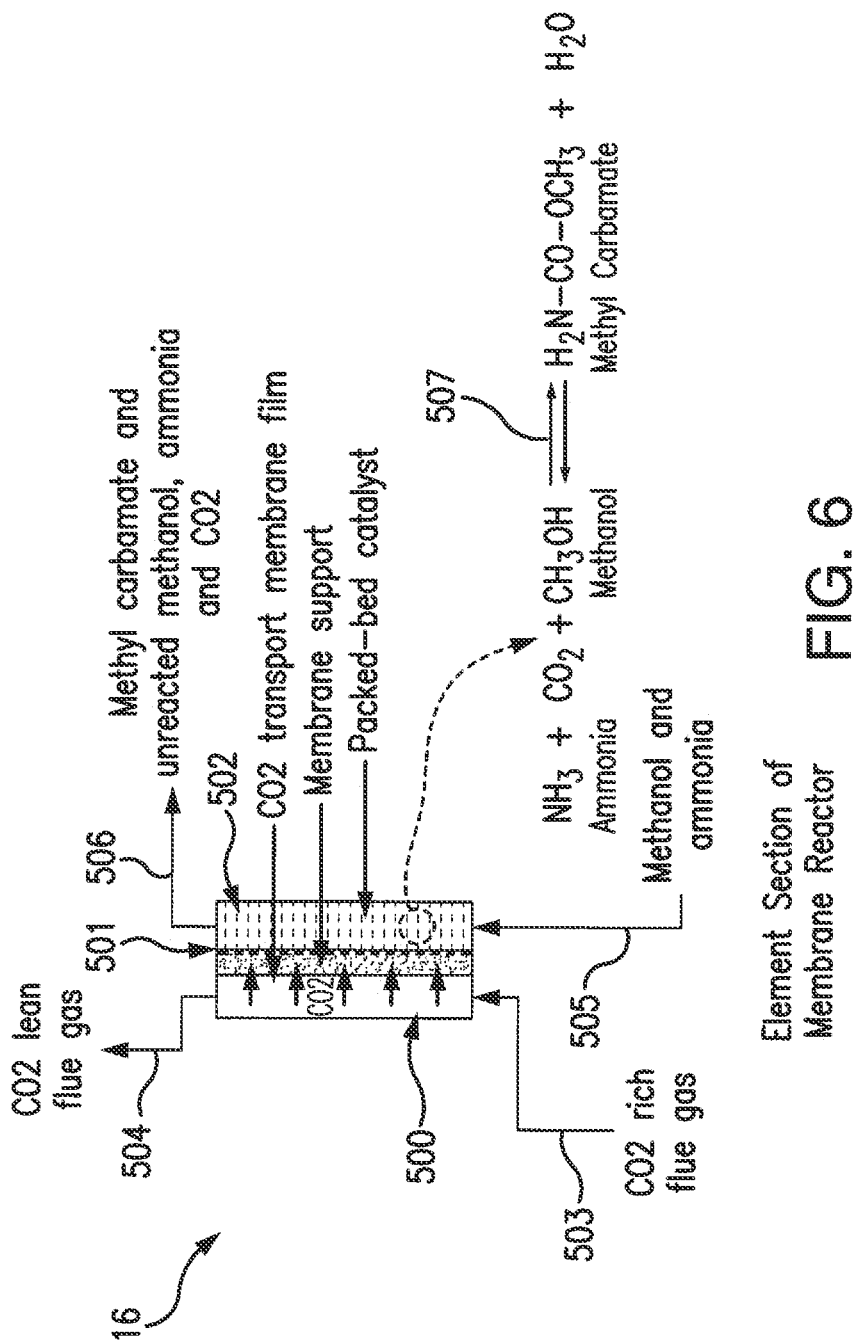
FIG. 6. is a membrane element with catalyst packed in the reactant flow channel of the membrane reactor.
Figure 7:
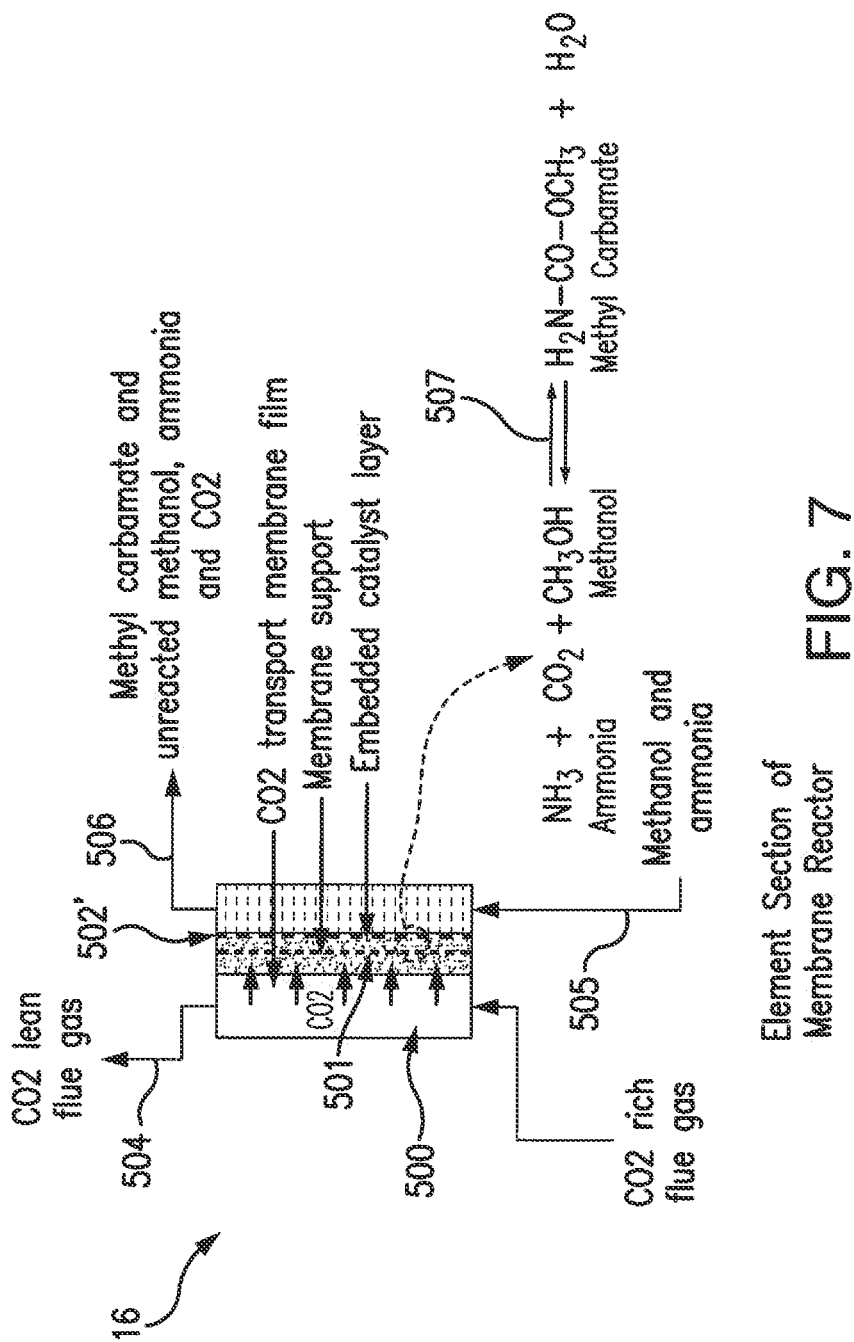
FIG. 7. is a membrane element with catalyst embedded on the membrane surface on the side of the reactant flow channel in the membrane reactor.

Referring FIGS. 6 and 7, there are two design concepts of the membrane reactor 16 which is shown in FIG. 1. FIG. 6 details an element section 500 of the membrane reactor 16. The membrane 501 consists of a membrane support and a carbon dioxide transport membrane film. Catalysts 502 are packed on the other side of the membrane through which reactants (ammonia and methanol) flow via the streamline 505. Flue gas containing carbon dioxide stream 503 flows through one side of the membrane. As carbon dioxide diffuses through the membrane 501, it reacts with methanol and ammonia in presence of a catalyst in the bulk flow region as depicted by the reaction equation 507. The resulting product stream exits via the streamline 506.

FIG. 7 represents an element section of the membrane reactor 16 (of FIG. 1) and differs from the element shown in FIG. 6 by inclusion of the embedded catalyst layer 502' instead of the packed-bed catalyst 502 of FIG. 6 on the membrane surface 501. As the carbon dioxide diffuses through the membrane 501, it reacts with methanol and ammonia at the membrane surface where catalysts 502' are embedded on the surface. The product methyl carbamate is then carried away by flowing methanol and exit via the streamline 506.

Figure 8:
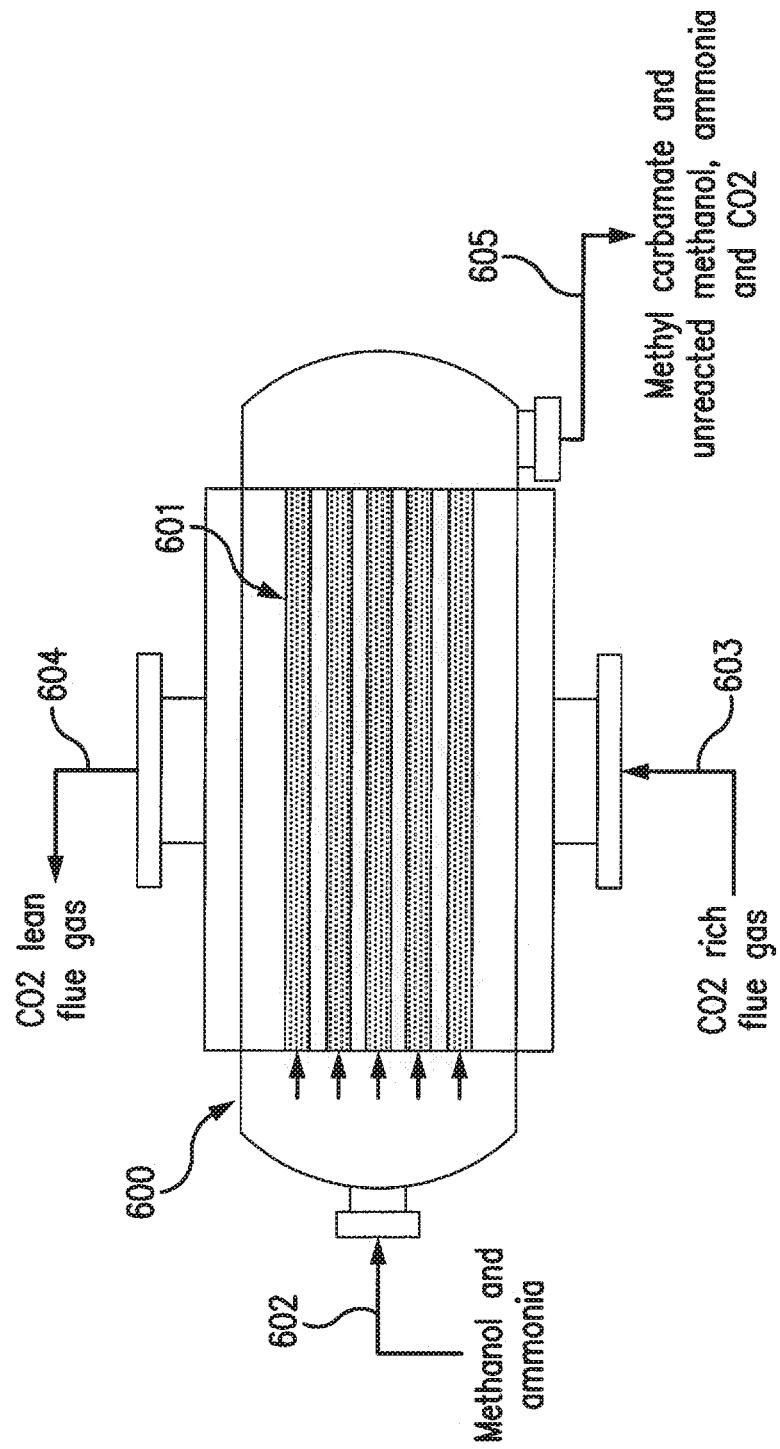
FIG. 8. is a schematic illustration of the membrane reactor with shell-and-tube module with cross-flow configuration.
Figure 9:
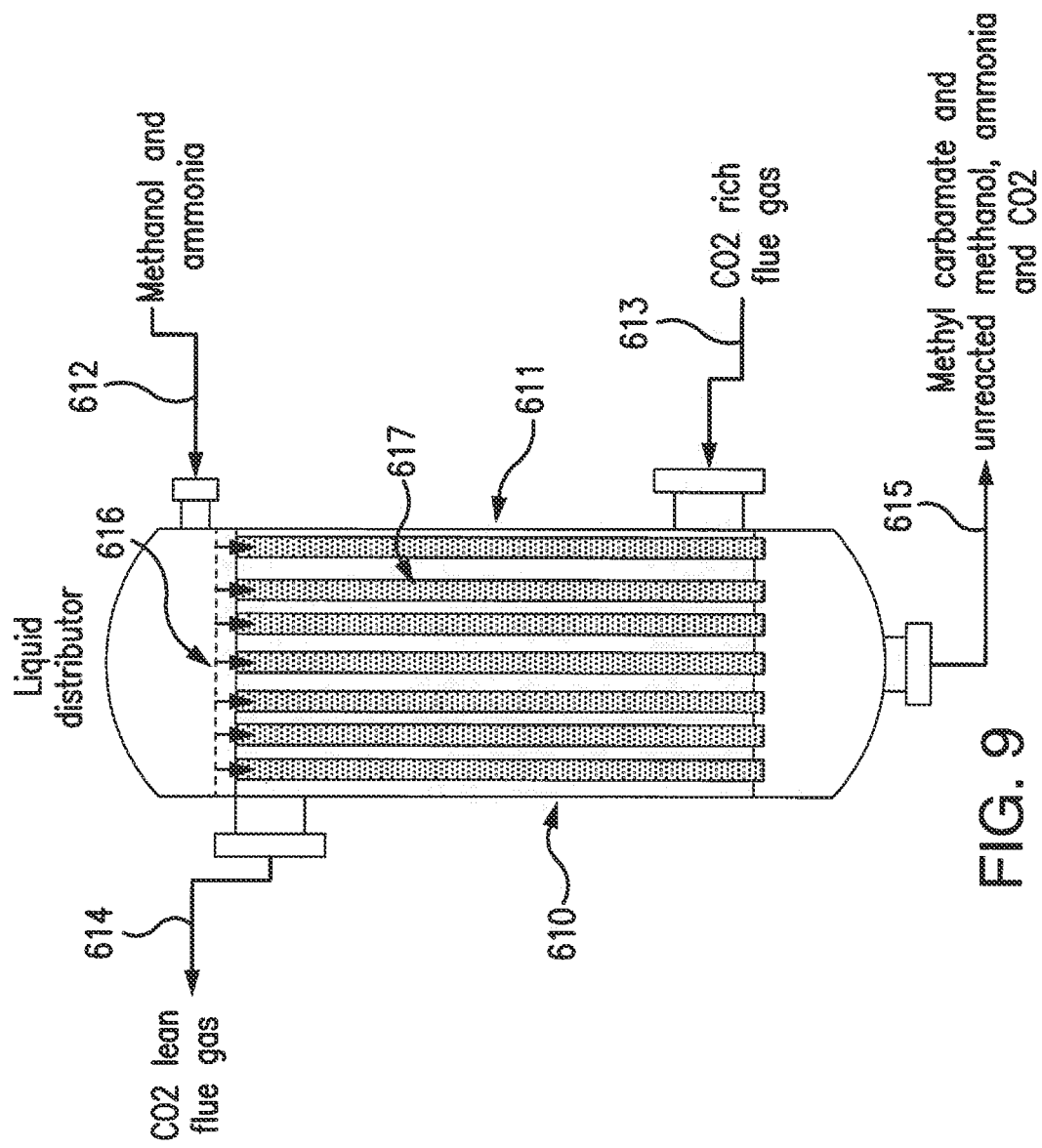
FIG. 9. is a schematic representation of the membrane reactor with shell-and-tube module with parallel-flow configuration.
Figure 10:
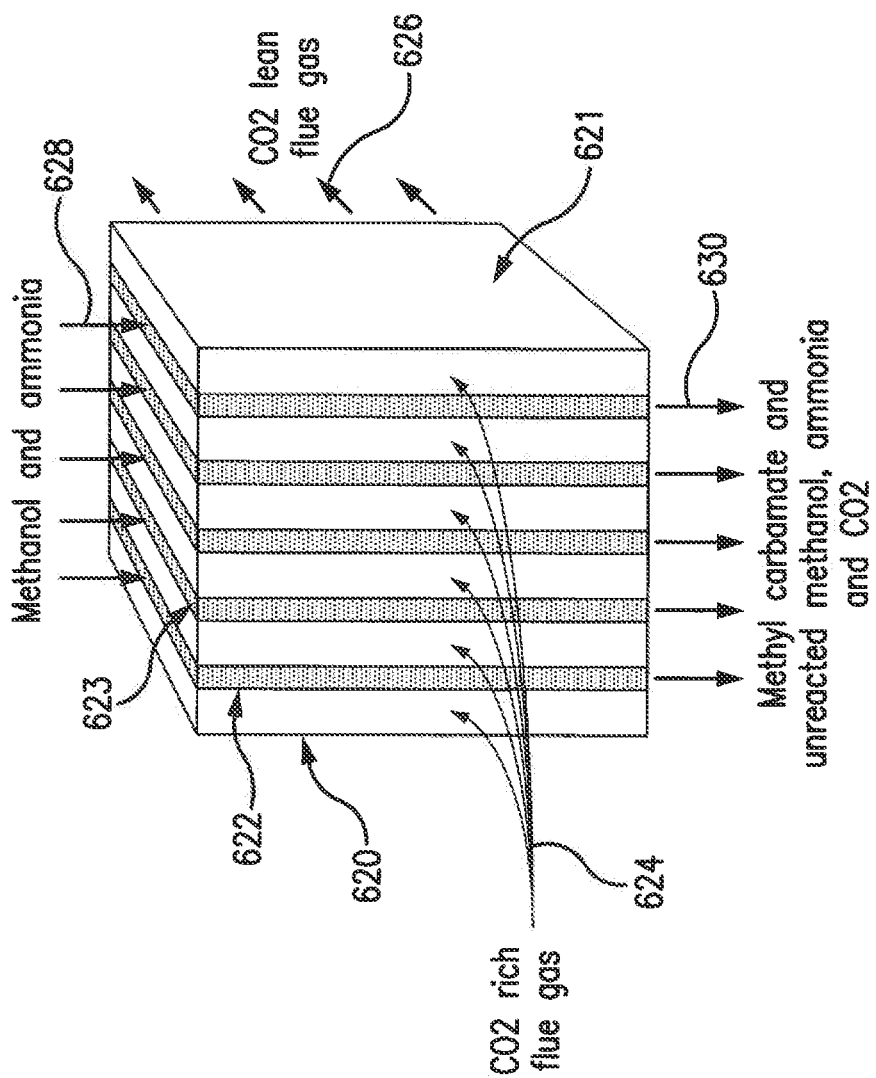
FIG. 10. depicts the membrane reactor with plate-and-frame module with cross-flow configuration.

Referring to FIGS. 8, 9 and 10, there are three different configurations of the membrane modules. FIG. 8 represents a shell-and-tube module 600 equipped with tubular membranes 601 with cross-flow of carbon dioxide flow stream 603. The tubular membrane 601 may have transport membrane film either inside or outside of the tube. Membrane tubes 601 are either packed with catalyst, as shown by FIG. 6, or embedded on the membrane surface, as shown in FIG. 7. Methanol and ammonia are fed in the module 600 via the line 602.

Some fraction of carbon dioxide is converted to products and the flow stream 604 exits as carbon dioxide lean flue gas.

The product stream consisting of methyl carbamate, some fraction of dimethyl carbonate, and unreacted ammonia, methanol and carbon dioxide, exits via flow stream 605 for further conversion.

FIG. 9 represents a shell-and-tube module 611 with tubular membranes 610, similar to that in FIG. 8, with parallel counter-flow carbon dioxide and reactants ammonia and methanol. Methanol and ammonia, either in the liquid or the vapor phase, as flow stream 612, are introduced from the top of the membrane module 611 and are distributed uniformly by a distributor 616 among all membrane tubes. Carbon dioxide is introduced via the flow streamline 613 on the shell side and it flows upward parallel to the tubular membrane tubes 610. Catalysts 617 are either packed inside tubes 610 or embedded on the membrane surface as shown in FIGS. 6 and 7. The carbon dioxide lean stream exits via the flow streamline 614, while methyl carbamate and unreacted methanol, ammonia and $CO_2$ exit via the line 615.

FIG. 10 represents an innovative concept of a plate-and-frame membrane module 620 used in the subject system. In the module 620, parallel plates 621 are assembled with alternate plate flow channels 622 which are packed with catalysts 623. Alternatively, catalysts may be embedded on the surface of the plates 621, as shown in FIGS. 6 and 7.

The carbon dioxide stream 624 enters from the side of the plate-and-frame membrane module 620 as shown by FIG. 10 and exists from the opposite side as flow stream 626. The flow stream 628 of ammonia is introduced from the top of the module 620 and flows down through the channels 622 holding catalysts 623.

Carbon dioxide diffusing through the membrane reacts with ammonia and methanol to produce methyl carbamate. The products stream 630 is withdrawn from the bottom of the membrane module 620.

Figure 11:
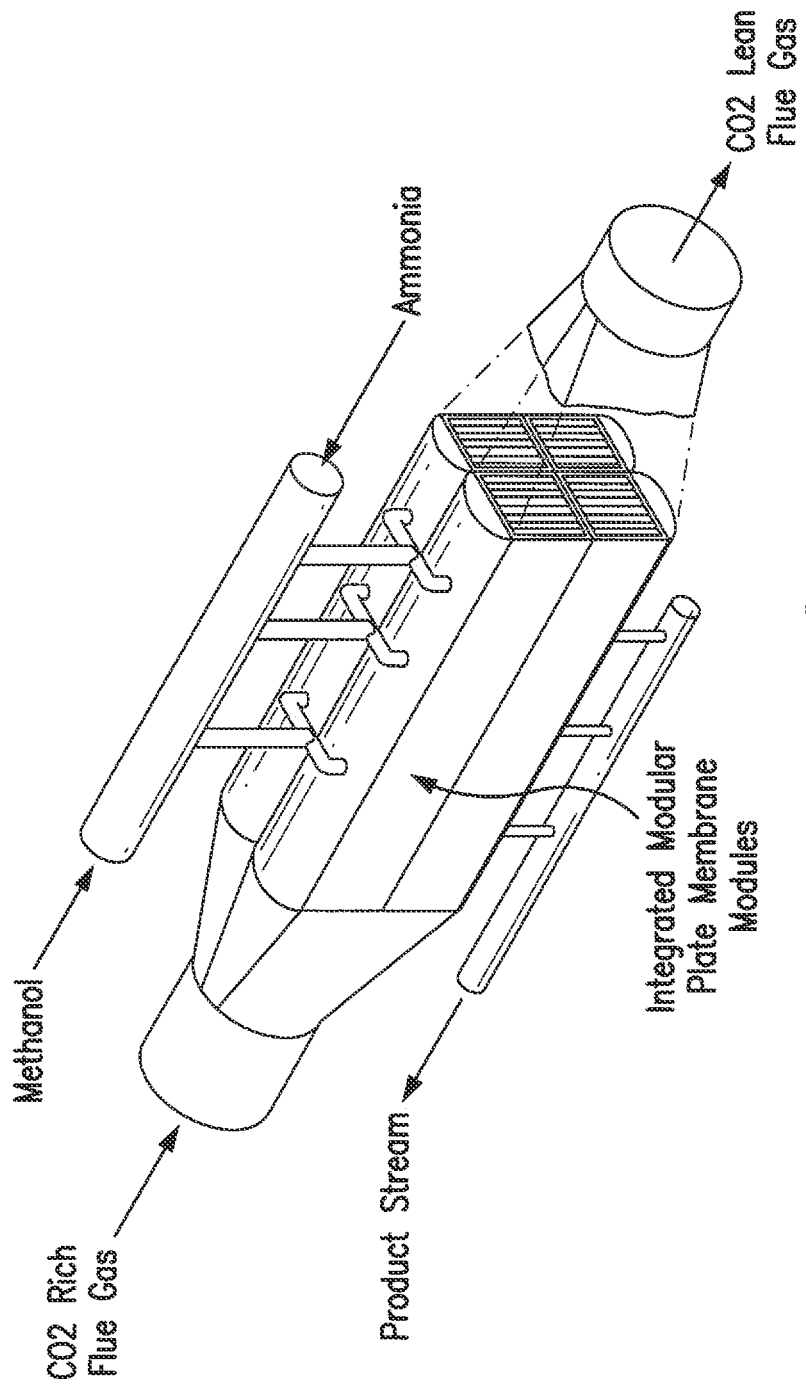
FIG. 11. is a schematic diagram of plate heat exchanger based on which plate-and-frame membrane reactor modules can be assembled.

The elemental section of plate-and-frame membrane module 620 can be assembled in a commercial-scale unit based on the conventional technology suitable for plate heat exchangers as shown, as an example, in FIG. 11. It is to be understood that commercial membrane modules including spiral-wound membrane modules or hollow-fiber membrane modules can also be used in the subject system. However, loading these types of commercial membranes with catalysts is difficult and such membrane modules cannot be built on a large scale required for converting flue gas carbon dioxide to alkyl carbonates.

For process streams illustrated in FIGS. 1, 2 and 3, the methanol/dimethyl carbonate azeotrope is shown to be broken with PerVap membrane unit on the distillate stage and between the two distillation columns, and the recovered methanol is recycled and fed to either singular or multiple side reactors. PerVap membrane units, as illustrated in FIGS. 1, 2 and 3 are commercially available and PerVap membranes, such as, for example, zeolite, cross-linked chitosan and highly fluorinated polymer membranes, may be used. The PerVap membrane units shown are for illustration purposes only, and other separation technologies for separating and recycle of the excess reactant methanol from the product stream may be used. Such separation methods may include molecular-sieve separation, pressure-swing adsorption (PSA), temperature-swing adsorption (TSA), liquid-liquid separation of immiscible liquid mixtures, liquid entrainment and heat integrated distillation.

The side reactors, main catalytic reactor and membrane reactors illustrated in FIGS. 1, 2 and 3 may be packed with commercial heterogeneous catalysts for each embodiment of the subject process.

Alternatively, homogeneous catalyst may be used which is dissolved in methanol. Such catalysts may be provided in the form of zinc oxide, zinc acetate dihydrate, zinc carbonate, zinc hydroxide, zinc nitrate hexahydrate, zinc chloride, lead nitrate, lead oxide, dialkyl tin oxide, dialkyl tin methoxide, or zinc oxide/urea organometallic complex. Alkyl may be any saturated carbon chain having less than 10 carbons. Different catalysts may be used on the individual membrane reactor, as well as the primary catalytic reactor, for direct conversion, and the individual side reactors.

The Table 1 below represents process parameters of a typical commercial plant cited in FIG. 1 with production capacity of 50,000 metric tons per year with product purity of 92 wt %.

TABLE 1

| Process Parameter | Value | Units |
|---|---|---|
| Dimethyl Carbonate (DMC) | 6,414 | kg/hr |
| Production Capacity | 50,000 | metric tons/year |
| Pure DMC | 6,408 | kg/hr |
| DMC Concentration | 99% | wt % |
| Product yield based on $CO_2$ Feedstock | 98% | |
| $CO_2$ feed stream | 43,667 | kg/hr |
| $CO_2$ concentration | 12% | |
| Fresh Methanol Flow Rate | 4,715 | kg/hr |
| Side Reactors | | |
| Temperature | 170 | °C. |
| Pressure | 27 | bar |
| First Distillation column | | |
| Reflux temperature | 81 | °C. |
| Bottom temperature | 220 | °C. |
| Pressure | 2.0 to 4.0 | bar |
| Second Distillation column | | |
| Reflux temperature | 136 | °C. |
| Bottom temperature | 250 | °C. |
| Pressure | 6.0 to 10.0 | bar |

TABLE 1-continued

| Process Parameter | Value | Units |
|---|---|---|
| $CO_2$ Merit Value | | |
| $CO_2$ Consumed | 0.49 | kg $CO_2$/kg DMC |
| $CO_2$ Generated by the process | 0.15 | kg $CO_2$/kg DMC |
| $CO_2$ Emissions of Methanol | 0.39 | kg $CO_2$/kg DMC |
| Net CO2 emission | 0.05 | kg $CO_2$/kg DMC |

The process consumes 0.49 kg of carbon dioxide per kg of dimethyl carbonate with net emissions of 0.05 kg carbon dioxide, as shown in Table 1. If the feed stock methanol is produced by renewable hydrogen and carbon dioxide, then there would be significant net permanent sequestration of carbon dioxide in the form of consumer product of alkyl carbonates.

This is compared to emissions of 1.76 kg carbon dioxide per kg of dimethyl carbonate produced by syngas-based commercial process. Table 2 represents the estimated global demands of dimethyl carbonate and corresponding potential abatement of carbon dioxide emissions. With full implementation of this invention process by 2050, there would be significant global abatement of carbon dioxide.

TABLE 2

| | DMC Market potentials, kTA* | | $CO_2$ Abatement Potentials, kTA* | |
|---|---|---|---|---|
| Applications | 2018 | 2030 | 2018 | 2030 |
| Polycarbonate production | 2,440 | 4,910 | 3,831 | 7,708 |
| Lithium-ion batteries | 45 | 350 | 71 | 550 |
| Solvent (replacing ketones) | 1,430 | 1,430 | 2,245 | 2,857 |
| Polyurethane production | 11,350 | 11,350 | 17,820 | 28,998 |
| Diesel-engine additive** | | 1,580,000 | | 2,480,000 |

*Thousand metric tons per year
**Based on government approval for pollution control Validation of Side Reactors The concept of side reactors has been experimentally validated in an integrated reaction column test unit. A flow redirecting device is installed in a packed column for directing liquid flowing down the packed column to the side reactor. The vapor rising from the bottom part of the column is directed to bypass of the side draw line of liquid. The product stream from the side reactor is returned to the next stage of the packing below the point of side draw. An integrated pump and surge tank system is used for controlling the liquid flow to the side reactor. The test data validated the performance of side reactor for the chemical system of conversion of $CO_2$ to dialkyl carbonates. ASPEN Plus® process analysis is validated with the experimental test data obtained with this integrated test unit where three side reactors are connected to the reaction column.

Kinetic Test Data

Figure 12:
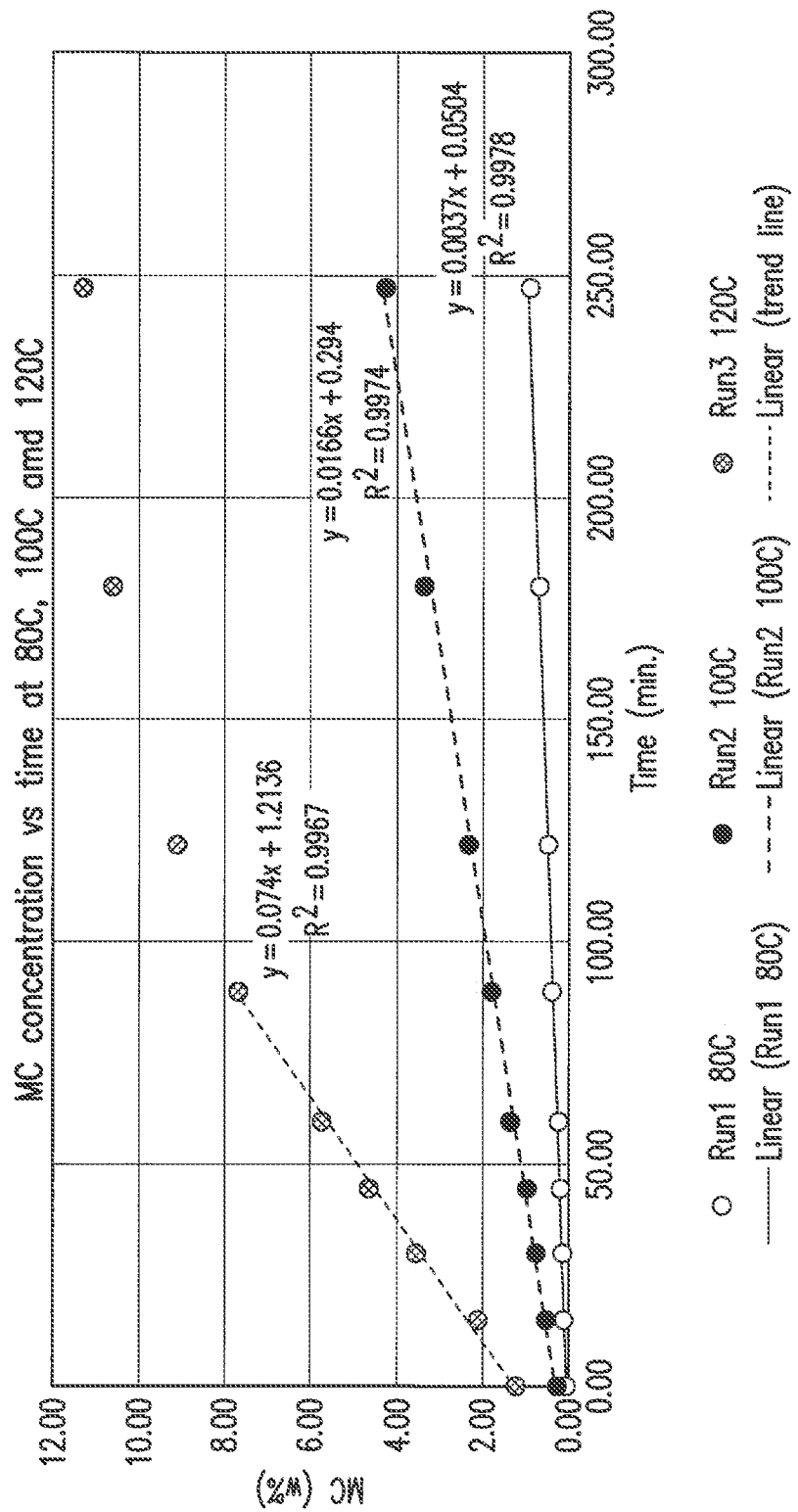
FIG. 12. is a figure depicting kinetic test data for conversion of urea to methyl carbamate.

Kinetic tests were performed with zinc oxide and zinc oxide-urea complex, which is found to be sparingly soluble in methanol. FIG. 12 shows conversion of urea to methyl carbamate at three reaction temperatures. The kinetic parameters are derived from such laboratory tests are validated with prototype test unit. The validated kinetic model for flow reactor is then incorporated into the process design using a commercial design software ASPEN Plus®.

Prototype Test Results

Figure 13:
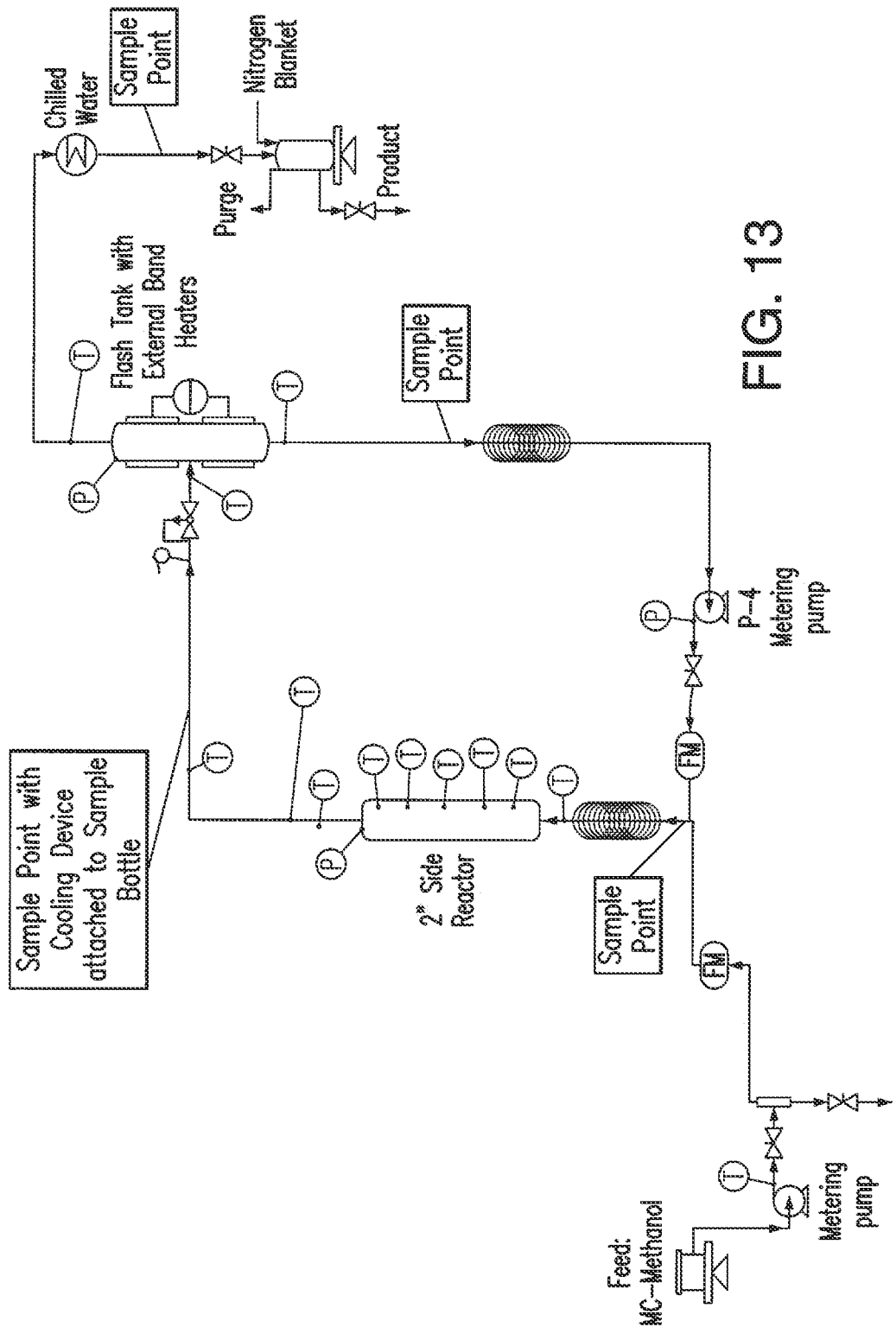
FIG. 13. is a schematic flow diagram of the prototype test unit for measuring performance parameters of side reactor.

FIG. 13 presents a flow diagram of the prototype test unit of a side reactor. This prototype test unit was used for conversion of methyl carbamate (MC) and urea to DMC. The kinetic parameters obtained with batch tests described above were incorporated into the ASPEN Plus® simulation model to predict the performance of side reactors. Table 3 shows the comparison of ASPEN Plus® predictions and test results of product composition. The quality and quantity of test parameter measurements were deemed adequate for validating the ASPEN Plus® model for simulation of the side reactor.

TABLE 3

| Parameters | 1.1.1.1 Test Run 1 | | 1.1.1.1 Test Run 2 | | 1.1.1.2 Test Run 3 | |
|---|---|---|---|---|---|---|
| | Test Data | Model Results | Test Data | Model Results | Test Data | Model Results |
| Feed Flowrate (g/min) | 37.6 | | 36.8 | | 45.3 | |
| Feed Composition (wt %) | | | | | | |
| Methanol | 76.4 | | 74.0 | | 69.3 | |
| Methyl Carbamate (MC) | 21.4 | | 21.2 | | 23.3 | |
| DMC | 0.37 | | 0.51 | | 0.36 | |
| Urea | 1.83 | | 4.31 | | 7.09 | |
| Product Composition (wt %) | | | | | | |
| Methanol | 78.2 | 75.4 | 74.6 | 71.8 | 70.8 | 66.1 |
| Methyl Carbamate (MC) | 20.6 | 22.9 | 22.8 | 25.4 | 24.8 | 29.9 |
| DMC | 0.66 | 0.82 | 0.83 | 1.00 | 0.55 | 0.80 |
| Urea | 0.53 | 0.26 | 1.80 | 0.58 | 3.90 | 1.53 |

Performance of PerVap Membrane

Figure 14:
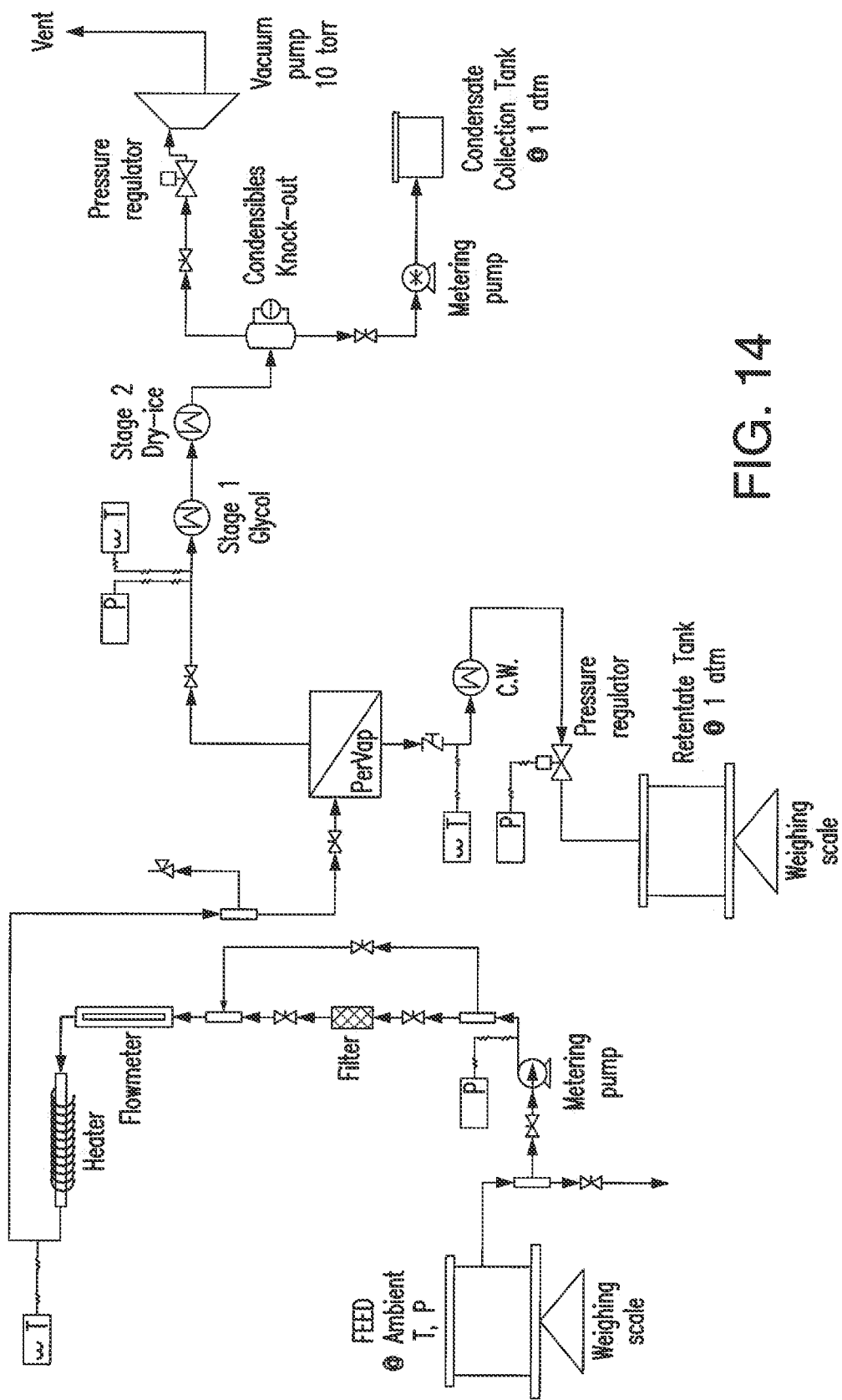
FIG. 14. is a schematic flow diagram of the test unit for measuring performance parameters of the PerVap membrane for selective separation of methanol from azeotrope of methanol and dimethyl carbonate.

FIG. 14 depicts schematic flow diagram of the test unit for measuring performance parameters of PerVap membrane for selective separation of methanol from azeotrope of methanol and dimethyl carbonate. Table 4 represents a summary of the performance parameters. Two series of tests were performed with liquid phase and vapor phase feed as shown in Table 4. In general high-purity methanol was separated as permeate with high-degree of selectivity. The PerVap membrane performance parameters were incorporated into the ASPEN Plus® process model.

Interfacing of Side Reactors with Distillation Column

Interfacing the side reactors with the distillation column without adverse impacts on the column performance requires careful design. This invention focuses on the following key criteria in design interface: 1) vapor flow should not be disturbed; 2) total or partial liquid flow to the side reactor using flow control valves should be employed; 3) liquid is returned to the next stage to a tray or packed column; 4) heat is recovered using a feed/effluent heat exchanger for the side reactor and the column may operate at different temperatures and pressures; and 5) interfacing design is based on commercially available hardware devices for minimizing operational risks.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A method for synthesis of dimethyl carbonate, comprising:
   (a) establishing a system including a reactor sub-system comprising a membrane reactor and a catalytic reactor operatively coupled to an output of said membrane reactor, and a distillation sub-system comprising a reaction distillation column, a product distillation column in a thermal coupling with said reaction distillation column, and a plurality of side reactors operatively coupled to said reaction distillation column of said distillation sub-system, said distillation sub-system being operatively coupled to said reactor sub-system,
   (b) capturing and supplying carbon dioxide ($CO_2$) into said membrane reactor of said reactor sub-system,
   (c) feeding methanol and ammonia into said membrane reactor of said reactor sub-system, and
   (d) reacting said carbon dioxide ($CO_2$) with said methanol and ammonia in said membrane reactor of said reactor

TABLE 4

| | Liquid Feed Rate mL/min | Feed Temp C. | Perm. Flux g/min | Composition, wt % | | | | | | Permeation Flux kg/m²/hr | MeOH/DMC Selectivity | Comments |
| | | | | Feed | | Retentate | | Permeate | | | | |
| ID | | | | MeOH | DMC | MeOH | DMC | MeOH | DMC | | | |
|---|---|---|---|---|---|---|---|---|---|---|---|---|
| Liquid Feed | | | | | | | | | | | | |
| TEST 1 | 4.0 | 95 | 0.51 | — | — | 67.3% | 32.7% | 95.9% | 4.1% | 6.1 | 11.4 | |
| TEST 2 | 4.0 | 95 | 1.04 | 65.0% | 35.0% | 64.9% | 35.1% | 95.5% | 4.5% | 12.5 | 11.5 | Broken O-ring |
| TEST 3 | 4.0 | 105 | 0.68 | 67.8% | 32.2% | 66.3% | 33.7% | 97.9% | 2.1% | 8.2 | 23.7 | |
| TEST 4 | 4.0 | 105 | 0.59 | 65.3% | 34.7% | 63.4% | 36.6% | 97.3% | 2.7% | 7.1 | 20.8 | |
| TEST 5 | 4.0 | 105 | 0.65 | 61.1% | 38.9% | 57.4% | 42.6% | 98.0% | 2.0% | 7.8 | 36.4 | |
| Vapor Feed | | | | | | | | | | | | |
| TEST 6 | 4.0 | 105 | 0.34 | 26.5% | 73.5% | 24.7% | 75.3% | 93.6% | 6.4% | 4.1 | 44.6 | |
| TEST 7 | 4.0 | 109 | 0.36 | 19.7% | 80.3% | 23.1% | 76.9% | 61.4% | 8.6% | 4.3 | 35.4 | |
| TEST 8 | 4.0 | 139 | 0.31 | 67.7% | 32.3% | 68.0% | 32.0% | 96.2% | 3.8% | 3.7 | 11.9 | |
| TEST 9 | 4.0 | 133 | 0.27 | 68.6% | 31.4% | 68.6% | 31.4% | 97.3% | 2.7% | 3.2 | 16.5 | |

Membrane area 0.005 m²  Selectivity, MeOH/DMC $$\alpha_{MeOH/DMC} = \frac{Y_{MeOH}/Y_{DMC}}{X_{MeOH}/X_{DMC}}$$

sub-system, thus forming a membrane reactor product comprising dimethyl carbonate, unreacted methanol, unreacted ammonia, and methyl carbamate, (e) feeding a membrane reactor product stream of said membrane reactor product formed in said membrane reactor of said reactor sub-system into said reaction distillation column of said distillation sub-system, (f) distilling said membrane reactor product in said reaction distillation column of said distillation sub-system to separate the unreacted ammonia from said membrane reactor product, recovering the unreacted ammonia from said reaction distillation column of said distillation sub-system, and recycling said unreacted ammonia to said membrane reactor of said reactor sub-system, (g) recovering said dimethyl carbonate, methyl carbamate, and unreacted methanol from said reaction distillation column of said distillation sub-system, feeding said recovered dimethyl carbonate, methyl carbamate, and unreacted methanol to a plurality of side reactors to form a concentrated dimethyl carbonate at an output of said reaction distillation column of said distillation sub-system, and recycling the concentrated dimethyl carbonate to an input of said reaction distillation column of said distillation sub-system, (h) separating unreacted methanol by distillation within said reaction distillation column of said distillation sub-system, recovering the separated unreacted methanol from said reaction distillation column of said distillation sub-system, and recycling the recovered methanol to said membrane reactor of said reactor sub-system, and (i) supplying a concentrated dimethyl carbonate stream of said concentrated dimethyl carbonate from the output of said reaction distillation column of said distillation sub-system to an input of said product distillation column of said distillation sub-system, distilling said concentrated dimethyl carbonate in said product distillation column of said distillation sub-system and recycling said distilled concentrated dimethyl carbonate stream via said product distillation column of said distillation system, thus obtaining a substantially pure dimethyl carbonate product.

2. The method of claim 1, further comprising:
in said step (b), capturing said carbon dioxide from combustion flue gas or a dilute industrial process stream for said reaction in said membrane reactor, and delivering high-purity carbon dioxide captured from the flue gas or the dilute industrial stream in said catalytic reactor, in said step (c), feeding a recycled ammonia and methanol into said catalytic reactor of said reactor sub-system, following said step (d), feeding a vapor phase of said membrane reactor product from said membrane reactor into said catalytic reactor of said reactor sub-system to further react an unreacted carbon dioxide remaining in said membrane reactor product with the recycled ammonia and methanol, thus producing a catalytic reactor product.

3. The method of claim 2, further comprising:
in said step (a), coupling a first permeation-vaporization (PerVap) membrane to an output of said membrane reactor and to an output of said catalytic reactor of said reactor sub-system, and following said step (d), directing said membrane reactor product stream from said output of said membrane reactor and from said output of said catalytic reactor product, respectively, to said first PerVap membrane to separate byproduct water therefrom and to form a PerVap membrane product stream containing methyl carbamate and ammonia.

4. The method of claim 3, further comprising:
in said step (a), operatively coupling said reaction distillation column to an output of said first PerVap membrane, and in said step (e), feeding said reaction distillation column of said distillation sub-system with said first PerVap membrane product stream from the output of said first PerVap membrane.

5. The method of claim 4, further comprising:
in said step (a), operatively coupling an ammonia rectification column to an upper output of said reaction distillation column, and
in said step (f), recycling said unrecovered ammonia from the upper output of said reaction distillation column to said ammonia rectification column, thus producing rectified ammonia.

6. The method of claim 5, further comprising:
recycling said rectified ammonia from said ammonia rectification column into said membrane reactor, and
reacting said rectified ammonia from said ammonia rectification column with said carbon dioxide captured in said step (b) and said methanol fed in said step (c) in said membrane reactor, thus producing methyl carbamate.

7. The method of claim 5, further comprising:
in said step (a), operatively coupling said plurality of side catalytic reactors to a bottom output of said reaction distillation column, and
in said step (g), recycling said methyl carbonate, methyl carbamate, and unreacted methanol from said bottom output of said reaction distillation column of said distillation sub-system through said plurality of side catalytic reactors, thus producing said concentrated dimethyl carbonate at outputs of said plurality of side catalytic reactors, and circulating said concentrated dimethyl carbonate from said outputs of the plurality of side catalytic reactors to said reaction distillation column at least twice, thus recovering said concentrated dimethyl carbonate.

8. The method of claim 7, further comprising:
in said step (a), configuring said reaction distillation column with a plurality of distillation stages,
in said step (g), drawing a mixture of dimethyl carbonate, methyl carbamate and unreacted methanol from at least a bottom distillation stage of said plurality of distillation stages of said reaction distillation column;
passing said drawn mixture of dimethyl carbonate, methyl carbamate and unreacted methanol through said plurality of side catalytic reactors for producing said concentrated dimethyl carbonate;
returning a mixture of dimethyl carbonate, methyl carbamate and unreacted methanol containing said concentrated dimethyl carbonate from said bottom output of said reaction distillation column to said reaction distillation column, and producing a vapor phase of said concentrated dimethyl carbonate in said reaction distillation column;
withdrawing said mixture containing said concentrated dimethyl carbonate in the vapor phase from a middle distillation stage of said plurality of distillation phases of said reaction distillation column; and
recycling a bottom product from said bottom output of said reaction distillation column to said plurality of side catalytic reactors, wherein said bottom product includes unreacted methyl carbamate.

9. The method of claim 8, further comprising:

in said step (a), operatively coupling at least one second PerVap membrane to said reaction distillation column, and in said step (h), condensing said mixture containing said concentrated dimethyl carbonate in the vapor phase, subsequently feeding said condensed mixture containing said concentrated dimethyl carbonate into said at least one second PerVap membrane for selective separation of said unreacted methanol from said condensed mixture containing concentrated dimethyl carbonate, recovering said separated unreacted methanol from said reaction distillation column, and recycling the recovered unreacted methanol to said membrane reactor of said reactor sub-system;

feeding a second PerVap product stream containing dimethyl carbonate from said at least one second PerVap membrane into said product distillation column to produce said substantially pure dimethyl carbonate product;

coupling at least one third PerVap membrane to an upper portion of said product distillation column; and condensing said second PerVap product stream and feeding said condensed second PerVap product stream from said product distillation column into said at least one third PerVap membrane for selective separation of methanol from said condensed second PerVap product stream.

10. The method of claim 9, further comprising:

operating said product distillation column at a high pressure for separation of methanol and dimethyl carbonate from an azeotropic mixture thereof; and recovering said substantially pure dimethyl carbonate product as a bottom product of said product distillation column.

11. The method of claim 1, where said reaction distillation column is equipped with thermally active trays disposed at selected locations of said reaction distillation column.

12. The method of claim 1, where said membrane reactor is configured to recover and concentrate carbon dioxide from a dilute carbon dioxide stream and includes at least one membrane module selected from a group consisting of: a membrane module having a plurality of membranes defining flow passages therebetween and catalysts packed in said flow passages, and a membrane module with catalysts embedded on a membrane surface for conversion of carbon dioxide to methyl carbamate by reacting with ammonia and methanol, and wherein said catalytic reactor is selected from a group consisting of: a trickle-bed reactor, a packed-bed upflow reactor, and a fluidized-bed reactor, said catalytic reactor being configured for conversion of captured high-concentration carbon dioxide to methyl carbamate by reacting with ammonia and methanol.

13. The method of claim 9, further comprising:

in said step (a), operatively coupling a condenser unit to said reaction distillation column, in said step (g), drawing a product mixture of ammonia, unreacted methanol and dimethyl carbonate from an upper stage of said plurality of distillation stages of said reaction distillation column;

condensing said ammonia and unreacted methanol in said condenser unit;

in said step (f), charging said product mixture to said ammonia rectification column, and charging said rectified ammonia from said ammonia rectification unit to said membrane reactor; and in said step (h), recycling said bottom product from said reaction distillation column to at least one of said plurality of side reactors or into said product distillation column of said distillation sub-system.

14. The method of claim 7, further comprising:

in said step (a), operatively coupling at least one side catalytic reactor of said plurality of side catalytic reactors to the bottom output of said reaction distillation column, and converting methyl carbamate drawn from said reaction distillation column to the concentrated dimethyl carbonate in said at least one side catalytic reactor.

15. The method of claim 14, further comprising:

feeding said concentrated dimethyl carbonate composition from said at least one side catalytic reactor into the product distillation column at a location in said product distillation column below a location where the product mixture is drawn to said at least one side catalytic reactor.

16. The method of claim 7, further comprising:

passing said concentrated dimethyl carbonate through a plurality of distillation stages in said product distillation column in a direction from a top distillation stage towards a lower distillation stage of said product distillation column.

17. The method of claim 14, further comprising:

circulating the concentrated dimethyl carbonate composition in the vapor phase from the output of said product distillation column to an input of said product distillation column for producing a highly-concentrated substantially pure dimethyl carbonate product.

* * * * *